(12) United States Patent  
Ashworth et al.

(10) Patent No.: US 7,176,195 B2
(45) Date of Patent: Feb. 13, 2007

(54) FUSED AZEPINE DERIVATIVES AND THEIR USE AS ANTIDIURETIC AGENTS

(75) Inventors: Doreen Ashworth, Southampton (GB); Gary R. W. Pitt, Hampshire (GB); Peter Hudson, Southampton (GB); Christopher Yea, Romsey (GB); Richard J. Franklin, Wokingham (GB); Graeme Semple, Molndal (SE); David Paul Jenkins, Morganstown (GB)

(73) Assignee: Ferring BV, Hoofddorp (NL)

( * ) Notice: Subject to any disclaimer, the term of this patent is extended or adjusted under 35 U.S.C. 154(b) by 204 days.

(21) Appl. No.: 10/311,301

(22) PCT Filed: Jun. 21, 2001

(86) PCT No.: PCT/GB01/02737

§ 371 (c)(1),
(2), (4) Date: Jun. 13, 2003

(87) PCT Pub. No.: WO02/00626

PCT Pub. Date: Jan. 3, 2002

(65) Prior Publication Data

US 2004/0038962 A1 Feb. 26, 2004

(30) Foreign Application Priority Data

Jun. 26, 2000 (GB) .................. 0015601.8

(51) Int. Cl.
- *A61P 7/12* (2006.01)
- *A61K 31/55* (2006.01)
- *C07D 487/00* (2006.01)
- *C07D 498/00* (2006.01)
- *C07D 513/00* (2006.01)

(52) U.S. Cl. .............. 514/211.09; 514/211.1; 514/213.01; 514/215; 514/221; 540/552; 540/567; 540/568; 540/573; 540/578; 540/580; 540/593

(58) Field of Classification Search ........... 514/211.09, 514/211.1, 213.01, 215, 221; 540/552, 567, 540/568, 573, 578, 580, 593
See application file for complete search history.

(56) References Cited

U.S. PATENT DOCUMENTS 6,664,249 B1 * 12/2003 Ashworth et al. ..... 514/211.09
2003/0087892 A1 * 5/2003 Ashworth et al. ..... 514/211.08

FOREIGN PATENT DOCUMENTS

| EP | 0 636 625 A2 | 2/1995 |
| GB | 2 355 454 A | 4/2001 |
| WO | WO 95 34540 A | 12/1995 |
| WO | WO 95/34540 A1 | 12/1995 |
| WO | WO 99 06403 A | 2/1999 |
| WO | WO 99 06409 A | 2/1999 |
| WO | WO 01 49682 A | 7/2001 |

OTHER PUBLICATIONS

Ogawa et al. "Orally Active Nonpeptide Vasopressin $V_2$ Receptor Antagonists: A Novel Series of 1-[4-(Benzoylamino) benzoyl]-2,3,4,5-tetrahydro-1H-benzazepines and Related Componds," J. Med. Chem., 39:3547-3555 (1996).

* cited by examiner

*Primary Examiner*—Brenda Coleman
(74) *Attorney, Agent, or Firm*—Foley & Lardner LLP

(57) ABSTRACT

Compounds according to general formulae (1 and 2), wherein $G^1$ is an azepine derivative and $G^2$ is a group according to general formulae (9–11) are new. Compounds according to the invention are vasopressin $V_2$ receptor agonists. Pharmaceutical compositions of the compounds are useful as antidiuretic agents

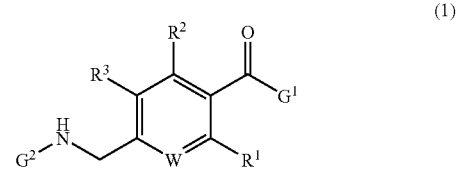

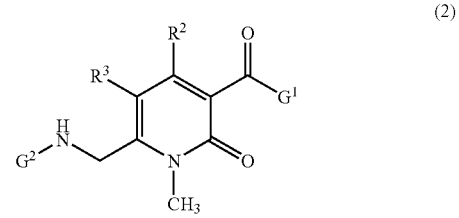

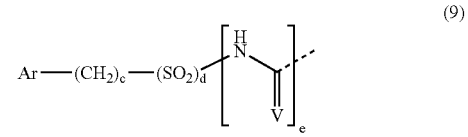

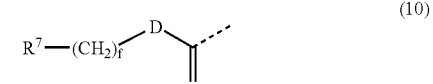

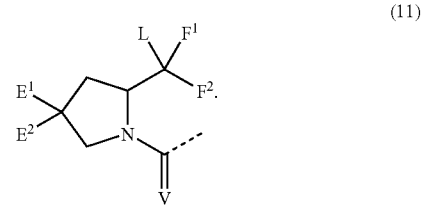

18 Claims, No Drawings

FUSED AZEPINE DERIVATIVES AND THEIR USE AS ANTIDIURETIC AGENTS

This application is the National Stage of International Application No. PCT/GB01/2737, filed Jun. 21, 2001.

FIELD OF INVENTION

The present invention relates to a class of novel chemical entities which act as agonists of the peptide hormone vasopressin. They reduce urine output from the kidneys and so are useful in the treatment of certain human diseases characterised by polyuria. They are also useful in the control of urinary incontinence and bleeding disorders.

BACKGROUND TO THE INVENTION

Vasopressin is a peptide hormone secreted by the posterior pituitary gland. It acts on the kidney to increase water retention and so reduce urine output. For this reason, vasopressin is alternatively known as "antidiuretic hormone". It also acts on the vasculature, where it produces a hypertensive effect. The cellular receptors that mediate these two actions have been characterised and shown to be different. The antidiuretic action is mediated by the type-2 vasopressin receptor, commonly called the $V_2$ receptor. Agents that can interact with the $V_2$ receptor and activate it in the same way as vasopressin are called $V_2$ receptor agonists (or simply $V_2$ agonists). Such agents will have an antidiuretic action. If these agents interact selectively with the $V_2$ receptor and not the other vasopressin receptor subtypes, then they will not have the hypertensive effect of vasopressin. This would be an important safety consideration and make such agents attractive for the treatment of human disease conditions characterised by polyuria (which is herein taken to mean excessive urine production).

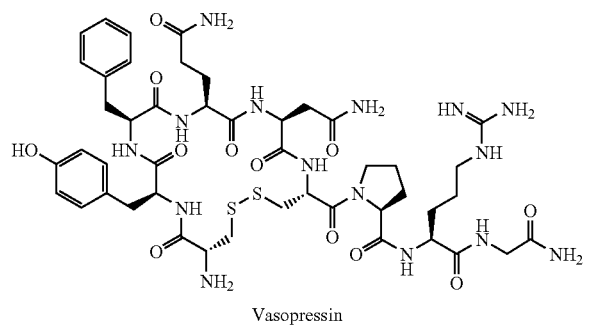

Vasopressin

In fact, such an agent is already in use in human therapy. Desmopressin (otherwise [1-desamino, D-Arg$^8$]vasopressin, Minirin™, DDAVP™, Octostim™) is a peptide analogue of vasopressin which is selectively an agonist at the $V_2$ receptor. It is used in the treatment of central diabetes insipidus, which is a condition that results from defective secretion of vasopressin. It is also employed in the control of nocturnal enuresis and may also be of use in the control of nocturia. However, desmopressin is not an ideal agent in all respects. Even the best current syntheses of the agent are lengthy, and desmopressin is not amenable to the most convenient of purification techniques such as crystallisation. Consequently, desmopressin is relatively expensive. It has a very low oral bioavailability, and there is some variability in this parameter.

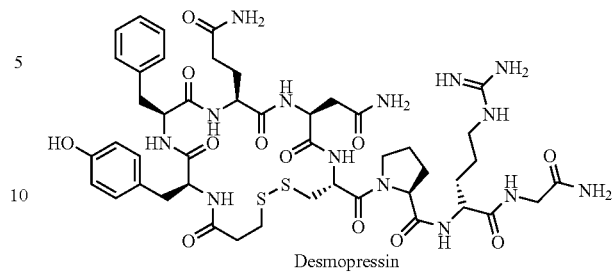

Desmopressin

Overall then, there is a recognised need for a selective vasopressin $V_2$ receptor agonist that is easy to prepare and purify, and that has a high and predictable oral bioavailability. Such properties are most likely to be obtained with a non-peptide compound. Examples of such compounds are disclosed by Ogawa et al. in International Patent Application PCT/JP96/03652 (WO97/22591), by Failli et al. in PCT/US98/15487 (WO99/06403), PCT/US00/00885 (WO00/46224), and PCT/US00/00358 (WO00/46227), by Dusza et al. in PCT/US98/15495 (WO99/06409), and by Steffan and Failli in PCT/US00/00886 (WO00/46225), and PCT/US00/00658 (WO00/46228). However the compounds disclosed in these documents are not ideal drug candidates. For example, some have only moderate selectivity for the $V_2$ receptor and many have only very limited oral bioavailability, probably because they are poorly soluble in aqueous media. The present invention provides compounds that show a better combination of properties.

The anti-diuretic action of desmopressin results in a decrease in the osmolarity of the blood, and this has been shown to be useful in th treatment and prophylaxis of sickle-cell disease. Besides its antidiuretic actions, desmopressin is used to increase the concentration in the blood of the coagulation proteins known as Faktor VIII and von Willebrand factor. In the clinical context, this makes desmopressin useful in the treatment of haemophilia A and von Willebrand's disease. Desmopressin has also been reported to show effects in the central nervous system. For example, it has been reported to be effective in the treatment of Tourette's disease and to be useful in the management of cocaine addiction. Similar applications would be open to the non-peptide agonists of the present invention.

SUMMARY OF THE INVENTION

The present invention relates to a series of compounds according to general formulae 1 and 2, and to salts and tautomers thereof, that are non-peptide agonists of vasopressin and which are selective for the $V_2$ receptor subtype.

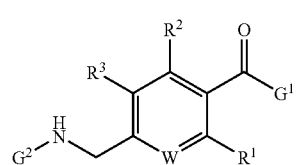

1

-continued

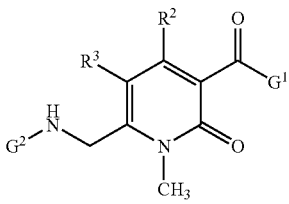

2 wherein:
W is either N or C—R⁴;
R¹–R⁴ are independently selected from H, F, Cl, Br, alkyl, CF₃, phenyl, OH, O-alkyl, NH₂, NH-alkyl, N(alkyl)₂, NO₂ and CN, or R² and R³ together can be —CH=CH—CH=CH—;
G¹ is a bicyclic or tricyclic fused azepine derivative selected from general formulae 3 to 8,

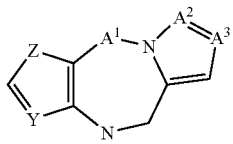

3

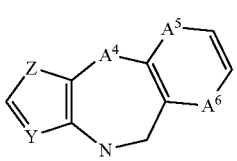

4

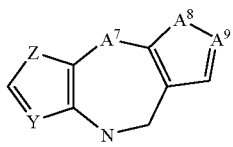

5

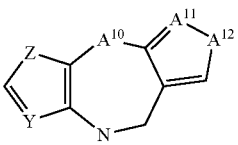

6

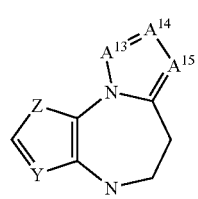

7

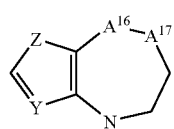

8 in which A¹, A⁴, A⁷ and A¹⁰ are each independently selected from CH₂, O and NR⁵;
A², A³, A⁹, A¹¹, A¹³, A¹⁴ and A¹⁵ are each independently selected from CH and N;
either A⁵ is a covalent bond and A⁶ is S, or A⁵ is N=CH and A⁶ is a covalent bond;

A⁸ and A¹² are each independently selected from NH, N—CH and S;
A¹⁶ and A¹⁷ are both CH₂, or one of A¹⁶ and A¹⁷ is CH₂ and the other is selected from CH(OH), CF₂, O, SO$_a$ and NR⁵;
R⁵ is selected from H, alkyl and (CH₂)$_b$R⁶;
R⁶ is selected from phenyl, pyridyl, OH, O-alkyl, NH₂, NH-alkyl, N(alkyl)₂, NO₂, CO₂H and CN;
a is 0, 1 or 2;
b is 1, 2, 3 or 4;
Y is CH or N;
Z is CH=CH or S; and
G² is a group selected from general formulae 9 to 11,

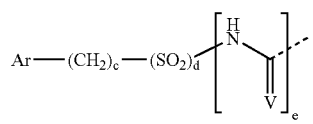

9

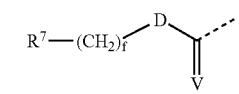

10

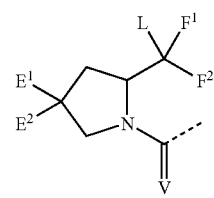

11 in which Ar is selected from phenyl, pyridyl, naphthyl and mono- or polysubstituted phenyl or pyridyl wherein the substituents are selected from F, Cl, Br, alkyl, OH, O-alkyl, NH₂, NH-alkyl, N(alkyl)₂, NO₂ and CN;
D is a covalent bond or NH;
E¹ and E² are both H, OMe or F, or one of E¹ and E² is OH, O-alkyl, OBn, OPh, OAc, F, Cl, Br, N₃, NH₂, NHBn or NHAc and the other is H, or E¹ and E² together are =O, —O(CH₂)$_g$O— or —S(CH₂)$_g$S—;
F¹ and F² are both H, or together are =O or =S;
L is selected from OH, O-alkyl, NH₂, NH-alkyl and NR⁹R¹⁰;
R⁷ is selected from H, alkyl, alkenyl and COR⁸;
R⁸ is selected from OH, O-alkyl, NH₂, NH-alkyl, N(alkyl)₂, pyrrolidinyl and piperidinyl;
R⁹ and R¹⁰ are both alkyl, or together are —(CH₂)$_h$— or —(CH₂)₂O(CH₂)₂;
V is O, N—CN or S;
c is 0 or 1;
d is 0 or 1;
e is 0 or 1;
f is 0, 1, 2, 3 or 4;
g is 2 or 3; and
h is 3,4 or 5,
provided that d and e are not both 0.

The invention further comprises pharmaceutical compositions incorporating these vasopressin agonists, which compositions are particularly useful in the treatment of central diabetes insipidus, nocturnal enuresis and nocturia.

DESCRIPTION OF THE INVENTION

In a first aspect, the present invention comprises novel 4-(aminomethyl)benzamide and 6(aminomethyl)nicotinamide derivatives according to general formulae 1 and 2.

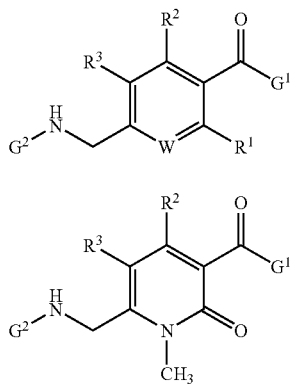

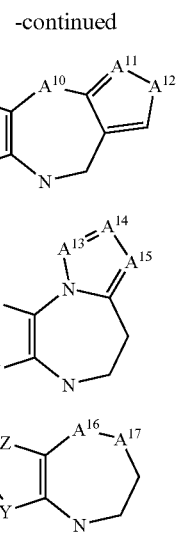

In general formula 1, W represents either a nitrogen atom (N) or a substituted carbon atom (C—$R^4$). The substituents $R^1$–$R^4$ are each independently selected from hydrogen (H), fluorine (F), chlorine (Cl) and bromine (Br) atoms, and alkyl, trifluoromethyl ($CF_3$), phenyl (Ph), hydroxyl (OH), alkoxy (O-alkyl), primary amino ($NH_2$), monoalkylamino (NH-alkyl), dialkylamino (N(alkyl)$_2$), nitro ($NO_2$) and cyano (CN) groups. Alternatively, $R^2$ and $R^3$ together can be —CH═CH—CH═CH— such that together with the ring to which they are attached they form a naphthalene, isoquinoline or isoquinolin-3one fused ring system. The relationship between the two general formulae above is clear when one considers the compound of general formula 1 in which W is nitrogen and $R^1$ is hydroxyl. The resulting 2-hydroxypyridine can also exist as its 2-pyridone tautomer. In this tautomeric form the nitrogen atom is able to carry a substituent equivalent to $R^4$, and such a compound is represented by general formula 2.

The group $G^1$ is a bicyclic or tricyclic fused azepine derivative selected from general formulae 3 to 8. It is joined to the carbonyl group of the parent molecule (1 or 2) through the nitrogen atom of the azepine ring common to all of 3 to 8, so as to form an amide bond.

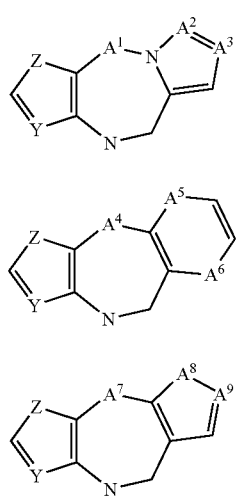

In these formulae, $A^1$, $A^4$, $A^7$ and $A^{10}$ each represent an oxygen atom (—O—) or a methylene (—$CH_2$—) or substituted imino (—$NR^5$—) group. $A^2$, $A^3$, $A^9$, $A^{11}$, $A^{13}$, $A^{14}$ and $A^{15}$ each represent a methine group (═CH—) or a nitrogen atom (═N—). Where two or more of these occur in the same group, each is independent of the others. Thus, for example, in formula 3, $A^2$ and $A^3$ may both be nitrogen, both methine, or one may be methine and the other nitrogen. $A^5$ and $A^6$ are chosen together such that either $A^5$ is a covalent bond and $A^6$ is a sulphur atom (—S—), to give a thiophene ring, or $A^5$ is a group —N═CH— and $A^6$ is a covalent bond to give a pyridine ring. $A^8$ and $A^{12}$ each represent an imino group (—NH—), an N-methyl imino group (—$NCH_3$—) or a sulphur atom (—S—). $A^{16}$ and $A^{17}$ may both represent a methylene group (—$CH_2$—) or one of $A^{16}$ and $A^{17}$ may represent a methylene group while the other represents a hydroxymethylene group (—CH(OH)—), a difluoromethylene group (—$CF_2$—), a substituted imino group (—$NR^5$—), an oxygen atom (—O—), or an optionally oxidised sulphur atom (—$SO_a$—), where a is zero, 1 or 2.

The group $R^5$ represents a hydrogen atom (H), an alkyl group, or a group —$(CH_2)_b R^6$, where b is 1, 2, 3 or 4. The group $R^6$ represents a group selected from phenyl, pyridyl, hydroxy (—OH), alkoxy (—O-alkyl), primary amino (—$NH_2$), mono- and dialkylamino (—NH-alkyl and N(alkyl)$_2$), nitro (—$NO_2$), carboxy (—$CO_2H$) and cyano (—CN) groups.

Y represents either a methine group (═CH—) or a nitrogen atom (═N—). Z represents either a sulphur atom (—S—) or a group —CH═CH—.

The group $G^2$ is selected from general formulae 9 to 11.

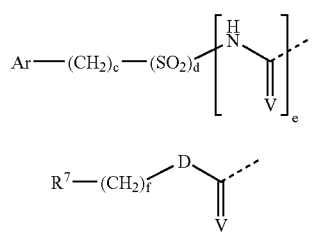

-continued

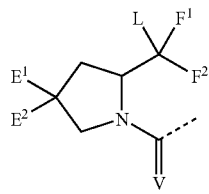

11

In these formulae, V represents a divalent residue selected from oxygen (=O) and sulphur (=S) atoms and a cyanimide (=N—CN) group.

In general formula 9, Ar represents an aromatic group selected from phenyl, pyridyl, naphthyl and mono— or polysubstituted phenyl and pyrdyl groups, wherein the substituents are selected from fluorine (F), chlorine (Cl) and bromine (Br) atoms and alkyl, hydroxy (—OH), alkoxy (—O-alkyl), primary amino (—NH$_2$), mono- and dialkylamino (—NH-alkyl and N(alkyl)$_2$), nitro (—NO$_2$), carboxy (—CO$_2$H) and cyano (—CN) groups. The values of c, d and e are independently zero or 1, provided that d and e are not both zero.

In general formula 10, D represents a covalent bond or an imino group (—NH—). The group $R^7$ represents a hydrogen atom (H), an alkyl or alkenyl group, or a group —COR$^8$, in which $R^8$ represents a hydroxy (—OH), alkoxy (—O-alkyl), primary amino (—NH$_2$) or mono- or dialkylamino (—NH-alkyl and N(alkyl)$_2$) group, or a cyclic amino group selected from pyrrolidinyl (—N(CH$_2$)$_4$) and piperidinyl (—N(CH$_2$)$_5$). The value of f is zero, 1, 2, 3 or 4.

In general formula 11, $E^1$ and $E^2$ represent either two monovalent atoms or groups, which may be the same or different, or together they represent a divalent atom or group. When $E^1$ and $E^2$ represent monovalent atoms or groups, these may both simultaneously be hydrogen (H) or fluorine (F) atoms or methoxy (—OMe) groups, or one may be a fluorine (F), chlorine (Cl) or bromine (Br) atom, or a hydroxy (—OH), alkoxy (—O-alkyl), benzyloxy (—OBn), phenoxy (—OPh), acetoxy (—OAc), azido (—N$_3$), primary amino (—NH$_2$), benzylamino (—NHBn) or acetamido (—NHAc) group and the other is a hydrogen atom (H). When $E^1$ and $E^2$ together represent a divalent atom or group, this may be an oxygen atom (=O) or an α,ω-dioxa- or dithiapolymethylene group (—O(CH$_2$)$_g$O— or —S(CH$_2$)$_g$S—), in which the value of g is either 2 or 3.

$F^1$ and $F^2$ may both represent a hydrogen (H) atom. Alternatively, they may together represent an oxygen (=O) or sulphur (=S) atom. L represents a group selected from hydroxy (—OH), alkoxy (—O-alkyl), primary amino (—NH$_2$) and monoalkylamino (—NH-alkyl) groups and —NR$^9$R$^{10}$, wherein either $R^9$ and $R^{10}$ each represent alkyl groups which may be the same or different, or together they represent a polymethylene group (—(CH$_2$)$_h$—) in which h can be 3, 4 or 5, or —(CH$_2$)$_2$O(CH$_2$)$_2$—.

As used herein, the term "alkyr" includes saturated hydrocarbon residues, including linear, branched and cyclic groups, with up to six carbon atoms. Examples of alkyl groups include, but are not limited to, methyl, ethyl, propyl, isopropyl, n-butyl, seo-butyl, isobutyl, tert-butyl, neopentyl and cyclohexyl groups.

The term "alkenyl" includes mono-unsaturated hydrocarbon residues, including linear, branched and cyclic groups, of between two and six carbon atoms. Examples of alkenyl groups include, but are not limited to, vinyl, 1-propenyl, allyl, 2-methyl-2-propenyl, 2-butenyl, 3-cyclopentenyl and 2,3-dimethyl-2-butenyl groups.

Certain compounds within the scope of the present invention may exist as tautomers. For example, when W is nitrogen and $R^1$ or $R^2$ is a hydroxy group, or when Ar is pyridyl further substituted by a hydroxy group, the resulting hydroxypyridine can exist as the pyridone tautomer. All such tautomers are considered to be within the scope of the present invention.

Certain compounds of general formula 1 are capable of forming salts with acids or bases. For example, compounds containing one or more basic nitrogen atoms can form addition salts with mineral and organic acids such as hydrochloric acid, sulphuric acid, phosphoric acid, acetic acid, trifluoroacetic acid, methanesulphonic acid, citric acid and benzoic acid. Compounds containing acidic groups can form salts with bases. Examples of such salts include the sodium, potassium, calcium, triethylammonium and tetraethylammonium salts. Furthermore, compounds that have both acidic and basic groups can form internal salts (zwiterions). Insofar as these salts are pharmaceutically acceptable, they are included within the scope of the invention.

A preferred embodiment of the invention is a compound according to general formula 1. More preferred is a compound according to general formula 1 in which W is C—R$^4$. Even more preferred is such a compound in which at least one of $R^1$–$R^4$ is other than hydrogen. Most preferred is a compound in which one of $R^1$–$R^4$ is methyl, chlorine or fluorine and the other three are hydrogen.

Another preferred embodiment of the invention is a compound according to general formula 2. More preferred is a compound according to general formula 2 in which $R^2$ and $R^3$ are both hydrogen.

Another preferred embodiment of the invention is a compound according to general formulae 1 or 2 in which $G^1$ is a group according to any of general formulae 3 to 7. More preferred is a compound in which Y is CH. Even more preferred is a compound in which Z is —CH=CH— so as to complete a benzenoid ring. Alternatively, Z may be S to complete a thiophene ring. When Y is N it is particularly preferred that Z be —CH=CH— so as to complete a pyridine ring.

Within the foregoing preferred embodiment, more preferred compounds are those wherein $G^1$ is a group according to general formula 3, particularly those wherein $A^1$ is CH$_2$ and both $A^2$ and $A^3$ are CH, and compounds wherein $G^1$ is a group according to general formula 6, particularly those wherein $A^{11}$ is CH and $A^{12}$ is S.

Another preferred embodiment of the invention is a compound according to general formulae 1 or 2 in which $G^1$ is a group according to general formula 8. More preferred is a compound in which one of $A^{16}$ and $A^{17}$ is CH$_2$. Even more preferred is a compound in which both $A^{16}$ and $A^{17}$ are CH$_2$.

Another preferred embodiment of the invention is a compound according to general formulae 1 or 2 in which $G^2$ is a group according to general formula 9. More preferred are those compounds wherein Ar is mono- or polysubstituted phenyl. Even more preferred are phenyl groups with at least two halogen (fluorine or chlorine) substituents. Most preferably, Ar is 2,6-difluorophenyl.

Another preferred embodiment of the invention is a compound according to general formulae 1 or 2 in which $G^2$ is a group according to general formula 10. More preferred are those compounds wherein $R^7$ is COR$^8$. Most preferred are those compounds wherein $R^8$ is N(alkyl)$_2$.

Another preferred embodiment of the invention is a compound according to general formulae 1 or 2 in which $G^2$ is a group according to general formula 11. More preferred are those compounds wherein $F^1$ and $F^2$ together are =O. Also preferred are those compounds wherein both $E^1$ and $E^2$ are H, or one is H and the other is O-alkyl. For those compounds wherein one of $E^1$ and $E^2$ is H and the other is O-alkyl, it is preferred that the stereochemistry at the $CE^1E^2$ centre be of the R absolute configuration. It is further preferred that the stereochemistry adjacent to the ring nitrogen atom be of the S absolute configuration. These configurations are illustrated below.

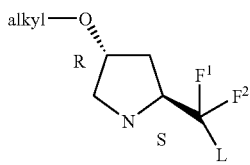

To the extent that the features of the foregoing preferred embodiments are independent of each other they may be combined in embodiments that are more preferred. Thus, highly preferred embodiments of the invention are those compounds that combine the preferred options for W and $R^1-R^4$ with the preferred options for $G^1$ and $G^2$.

A most preferred embodiment of the invention is a compound selected from the following.

1-(4-[3(2-Chloro-6-fluorophenyl)ureidomethyl]-3-methyl-benzoyl)-2,3,4,5-tetrahydro-1H-1-benzazepine 1-(4-[3-(2,6-Difluorophenyl)ureidomethyl]-3-methylbenzoyl)-5-(3-pyridyl)methyl-2,3,4,5-tetrahydro-1H-1,5-benzodiazepine 1-(3-Chloro-4-[3-(2-chloro-6-fluorophenyl)ureidomethyl]benzoyl)-5-ethyl-2,3,4,5-tetrahydro-1H-1,5-benzodiazepine 4-(3-Chloro-4-[3-(2,6-difluorophenyl)ureidomethyl]benzoyl)-5,6,7,8-tetrahydrothieno[3,2-b]azepine 1-(3-Chloro-4-(3-(methyloxycarbonyl)propanoylaminomethyl)benzoyl)-2,3,4,5-tetrahydro-1-benzazepine 1-(2-Methyl-4-(5-(3-pyridylmethyl)-2,3,4,5-tetrahydro-1,5-benzodiazepin-1-ylcarbonyl)benzyl)-3-(methyloxycarbonylmethyl)urea 1-(2-Methyl-4-(2,3,4,5-tetrahydro-1-benzazepin-1-ylcarbonyl)benzylcarbamoyl)-L-proline-N,N-dimethylamide (4R)-4-Hydroxy-1-(2-methyl-4-(2,3,4,5-tetrahydro-1-benzazepin-1-ylcarbonyl)benzyl-carbamoyl)-L-proline-N,N-dimethylamide (4R)-1-(3-Chloro-4-(2,3,4,5tetrahydro-1-benzazepin-1-ylcarbonyl)benzylcarbamoyl)-4-methoxy-L-proline-N,N-dimethylamide (4R)-1-(2-Chloro-4-(2,3,4,5-tetrahydro-1-benzazepin-1-ylcarbonyl)benzylcarbamoyl)-4-methoxy-L-proline-N,N-dimethylamide (4R)-4-Benzyloxy-1-(2-methyl-4-(2,3,4,5-tetrahydro-1-benzazepin-1-ylcarbonyl)benzyl-carbamoyl)-L-proline-N,N-dimethylamide (4R)-4-Methoxy-1-(2-methyl-4-(2,3,4,5-tetrahydro-1-benzazepin-1-ylcarbonyl)benzyl-carbamoyl)-L-proline-N,N-dimethylamide (4R)-4-Methoxy-1-(3-methyl-4-(2,3,4,5-tetrahydro-1-benzazepin-1-ylcarbonyl)benzyl-carbamoyl)-L-proline-N,N-dimethylamide (4R)-1-(2-Chloro-4-(5,6,7,8-tetrahydro-4H-thieno[3,2-b]azepin-4-ylcarbonyl)benzyl-carbamoyl)-4-methoxy-L-proline-N,N-dimethylamide (4R)-1-(4-(10,11-Dihydro-5H-pyrrolo[2,1-c](1,4)benzodiazepin-10-ylcarbonyl)-2-methyl-benzylcarbamoyl)-4-methoxy-L-proline-N,N-dimethylamide (4R)-1-(2-Chloro-4-(10,11-Dihydro-5H-pyrrolo[2,1-c](1,4)benzodiazepin-10-ylcarbonyl)-benzylcarbamoyl)-4-methoxy-L-proline-N,N-dimethylamide (4R)-1-(4-(10,11-Dihydro-5H-pyrrolo[2,1-c](1,4)benzodiazepin-10-ylcarbonyl)-2-methyl-benzylcarbamoyl)-4-methoxy-L-proline-N,N-dimethylthioamide Within this set of compounds, two which show an optimal balance of properties are 1-(2-methyl-4-(2,3,4,5-tetrahydro-1-benzazepin-1-ylcarbonyl)benzylcarbamoyl)-L-proline-N,N-dimethylamide and (4R)-4-hydroxy-1-(2-methyl-4-(2,3,4,5-tetrahydro-1-benzazepin-1-ylcarbonyl) benzylcarbamoyl)-L-proline-N,N-dimethylamide.

The present invention further comprises pharmaceutical compositions that include at least one compound according to the foregoing description as an active constituent. The composition may also include a second pharmacological agent such as a spasmolytic or a potassium channel blocker, these agents being known in the art to ameliorate bladder dysfunction. Preferably, the composition includes only one active constituent. The composition will include excipients selected from binding agents, bulking agents, dispersants, solvents, stabilising agents and the like, such excipients being generally known in the art.

The excipients used will depend on the intended nature of the formulation, which will, in turn, depend on the intended route of administration. Administration may be oral, transmucosal (such as sublingual, buccal, intranasal, vaginal and rectal), transdermal or by injection (such as subcutaneous, intramuscular and intravenous). Oral administration is generally preferred. For oral administration, the formulation will be a tablet or capsule. Other formulations include dry powders, solutions, suspensions, suppositories and the like.

In a further aspect, the present invention is a method of treating or controlling certain human physiological dysfunctions. This method comprises the administration to the person in need of such treatment of an effective amount of a pharmaceutical composition, which composition contains a compound according to the foregoing description as an active constituent The compounds act to reduce urine output, and so the method of the invention can be applied to all conditions in which elevated urine output is a contributory factor. The compounds also increase the production of the blood coagulation proteins known as Factor VIII and von Willebrand factor, and so the treatment of bleeding disorders can be undertaken.

In a preferred embodiment, the condition treated is central diabetes insipidus. This is a condition caused by an inability of the body to produce and secrete physiologically active vasopressin, with the result that water re-uptake is greatly reduced and large volumes of urine are produced.

In another preferred embodiment, the condition treated is nocturnal enuresis. This is defined as bladder emptying while the individual is sleeping. It is a condition that mainly affects children and a number of factors may be involved in its etiology.

In another preferred embodiment, the condition treated is nocturia. This is defined as production of sufficient urine during the night to require the individual to wake and empty his (or her) bladder. Again, this condition may be the result of a number of factors.

In another preferred embodiment, the condition treated is incontinence. This condition is characterised, in part, by reduced bladder capacity and control such that involuntary urination occurs unless the bladder is emptied frequently.

Incontinence has been divided into two conditions, stress incontinence and urge incontinence. A number of etiological factors are thought to be involved. Treatment according to the invention is particularly useful for delaying the need for bladder emptying ("voiding postponement") in order to allow the incontinent subject a dry period of a few hours (such as up to four hours). Such voiding postponement may also be useful for the non-incontinent population, for example for people obliged to remain in meetings for extended periods.

In another preferred embodiment, the condition treated is haemophilia A or von Willebrand's disease. This is a condition in which Factor VIII or von Willebrand factor production is reduced and the individual suffers from prolonged bleeding.

In another preferred embodiment, the composition is administered prior to surgery (including dental surgery) to increase the coagulability of the blood and so reduce perioperative blood loss.

The administration of the compositions of the present invention will generally be under the control of a physician. The physician will determine the amount of composition to be administered and the dosing schedule, taking into account the patient's physical condition and the therapeutic goals. For an adult diabetes insipidus patient, a typical dose might be between 50 mg and 1 g of the active compound per day, taken as a single tablet or as up to four tablets throughout the day. For routes of administration other than the oral route, the amount of compound will be reduced, since non-oral routes tend to be more efficient in terms of delivering therapeutic agents into the systemic circulation. For the treatment of von Willebrand's disease and haemophilia A, the amount of compound may need to be higher than for the treatment of diabetes insipidus.

The compounds of the present invention can be prepared using methods generally known in the art. The compounds of general formulae 1 and 2 can be considered to be composed of three linked fragments, $G^1$, $G^2$ and the central aromatic moiety (which will be referred to here as the "core"). Reagents corresponding to the three fragments will generally be prepared separately and then combined at a late stage in the synthesis.

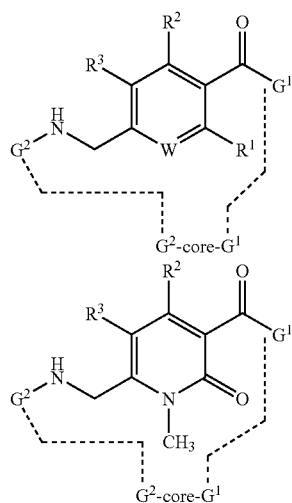

Some instances of the various groups and substituents might be incompatible with this assembly and so will require the use of protecting groups. The use of protecting groups is well known in the art (see for example "Protective Groups in Organic Synthesis", T. W. Greene, Wiley-Interscience, 1981). Particular groups that may require protection are amines (protected as amides or carbamates), alcohols (protected as esters or ethers) and carboxylic acids (protected as esters). For the purposes of this discussion, it will be assumed that such protecting groups as are necessary are in place.

The three fragments can be combined according to two strategies to give the compounds of formulae 1 and 2. In the first, the fragments corresponding to $G^1$ and the core are linked to give a fragment corresponding to core-$G^1$, which is then combined with fragment $G^2$. In the second, the fragments the fragments corresponding to the core and $G^2$ are linked to give a fragment corresponding to $G^2$-core, which is then combined with fragment $G^1$. The ch mistry involved in the condensation of fragment $G^1$ with the cor fragment, and that involved in the condensation of the core fragment with fragment $G^2$, will be the same whichever strategy is followed.

Formaton of Fragment Core-$G^1$

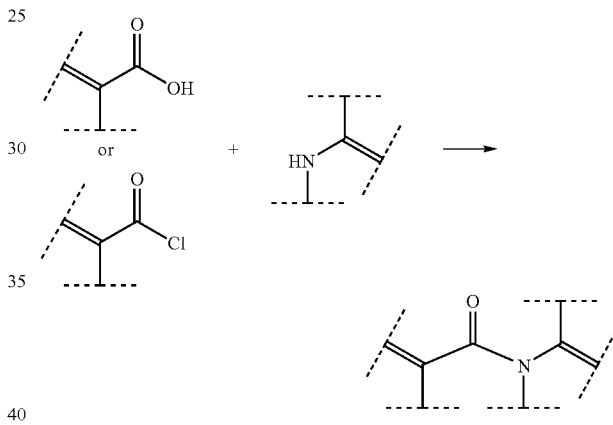

The synthesis of this fragment requires the formation of an amide bond between the two moieties. Reactions of this type are well known in the art. Most conveniently, an acid chloride corresponding to the core fragment may be allowed to react with the free secondary amino group of the $G^1$ azepine ring. Such a reaction generally is performed in an aprotic solvent such as dichloromethane or dimethylformamide at or slightly below room temperature. A tertiary amine base such as triethylamine or dimethylaminopyridine is usually added. Alternatively, the carboxylic acid corresponding to the core fragment may be condensed with the secondary amino group using one of the many reagents that have been developed for the formation of amide bonds in the field of peptide chemistry. Examples of such reagents include DCC (dicyclohexylcarbodiimide), BOP ((benzotriazol-1-yloxy)tris(dimethylamino)phosphonium hexafluorophosphate), PyBOP® ((benzotriazol-1-yloxy)tripyrrolidinophosphonium hexafluorophosphate), PyBroP® (bromotripyrrolidino-phosphonium hexafluorophosphate) and HBTU (O-(benzotriazol-1-yl)-N,N,N',N'-tetramethyluronium hexafluorophosphate). Other reagents are also known. The details of the synthetic method will depend on the particular reagent selected, but will generaly involve the use of an aprotic solvent and a tertiary amine base, as described above. Either the reagent is added to a mixture of the carboxylic acid and the azepine, or the carboxylic acid and the reagent are premixed to form a reactive intermediate (which is not isolated) to which is added the azepine.

Formation of Fragment $G^2$-core

Depending on the nature of $G^2$, the $G^2$-core bond can be part of an amide or thioamide, a sulphonamide, a urea or thiourea, a sulphonylurea or sulphonylthiourea, or a cyanoamidine, cyanoguanidine or sulphonylcyanoguanidine. The chemistry involved in the preparation of the G2-core bond will be different for each of these.

(i.a) Amides {$G^2$=10, D=Covalent Bond, V=O}

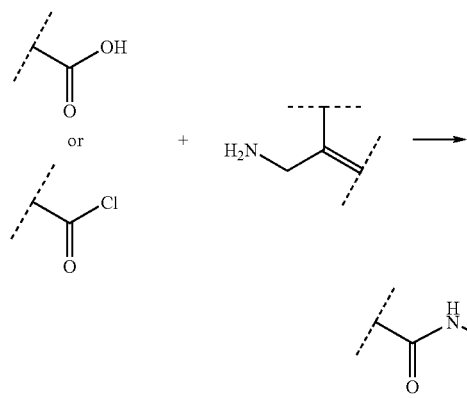

These compounds can be formed by the reaction of a carboxylic acid or acid chloride corresponding to fragment $G^2$ with the primary amino group of the core fragment. Conditions for the reaction will generally be similar to those described for the formation of the core-$G^1$ bond, except that the primary amine is more reactive than the azepine nitrogen and so lower temperatures and shorter reaction times may be used.

(i.b) Thioamides {$G^2$=10, D=covalent bond, V=S}

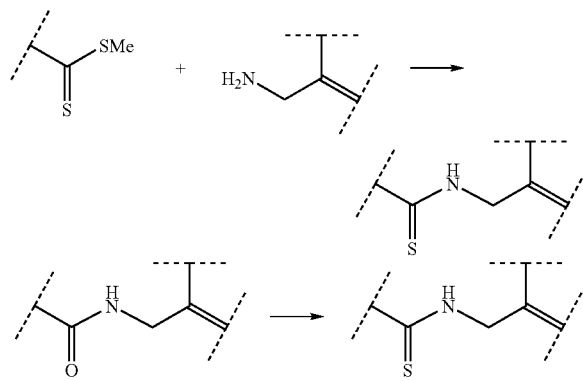

These compounds can be formed by the reaction of a suitable thiocarbonyl compound such as a dithioester ($RCS_2R'$) with the primary amine in a manner analogous to that described for the corresponding amides above. Alternatively, they may be prepared from the corresponding amides (V=O) by reaction with Lawesson's reagent.

(ii) Sulphonamides {$G^2$=9, d=1, e=Zero}

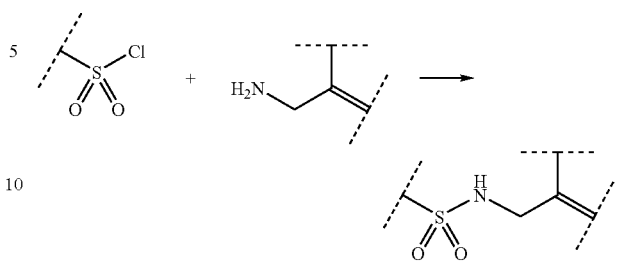

These compounds are generally prepared by the reaction of the sulphonyl chloride corresponding to the $G^2$ fragment with the primary amine of the core fragment. The reaction is generally performed under conditions similar to those described above for the reaction of a carboxylic acid chloride with the primary amine that gives the amides.

(iii.a) Ureas {$G^2$=9, d=Zero, e=1, V=O; $G^2$=10, D=NH, V=O; $G^2$=11, V=O}

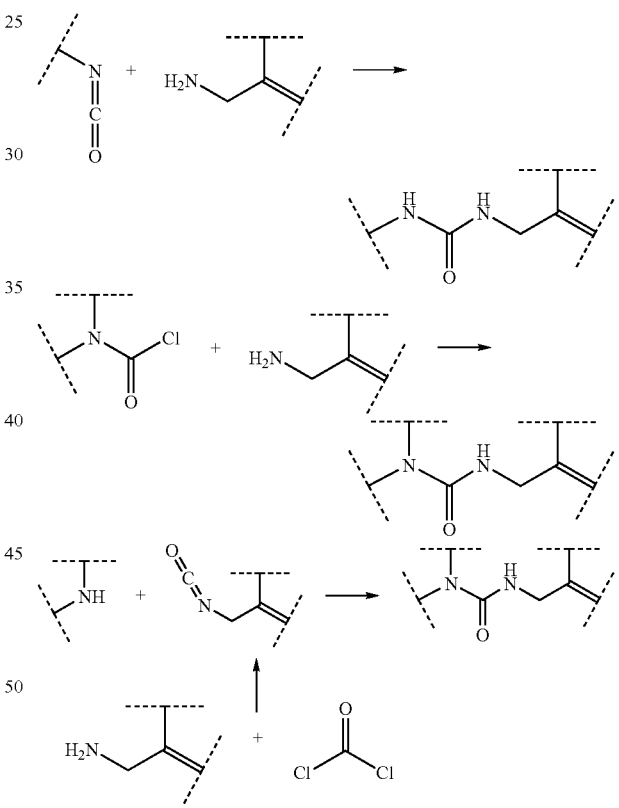

These compounds can be prepared by the reaction of an amine with an isocyanate or an equivalent thereof. Due to the symmetry of the urea functional group, there is the possibility to choose which component acts as the amine and which as the isocyanate. Most simply, when $G^2$ is a group according to 9 or 10, the corresponding isocyanate is readily accessible. It can conveniently be reacted with the primary amine of the core fragment in an aprotic solvent without the need for additional reagents. When $G^2$ is a group according to 11, the isocyanate is not available, and the carbamoyl chloride can be used in its place. The carbamoyl chloride is generally prepared immediately prior to use by treating the corresponding secondary amine with phosgene or an equivalent reagent such as diphogene or triphogene. Alternatively, the use of carbonyl diimidazole leads to the formation of a carbamoyl imidazole derivative that can be used in place of the carbamoyl chloride. The reaction of the carbamoyl chloride with the primary amine generally requires the addition of a tertiary amine base to neutralise the hydrogen chloride formed.

In some cases, it may be preferable to treat the primary amine corresponding to the core fragment with phosgene (or carbonyl diimidazole) to form an isocyanate that can subsequently be reacted with the primary or secondary amine corresponding to the $G^2$ fragment.

(iii.b) Thioureas {$G^2$=9, d=Zero, e=1, V=S; $G^2$=10, D=NH, V=S; $G^2$=11, V=S}

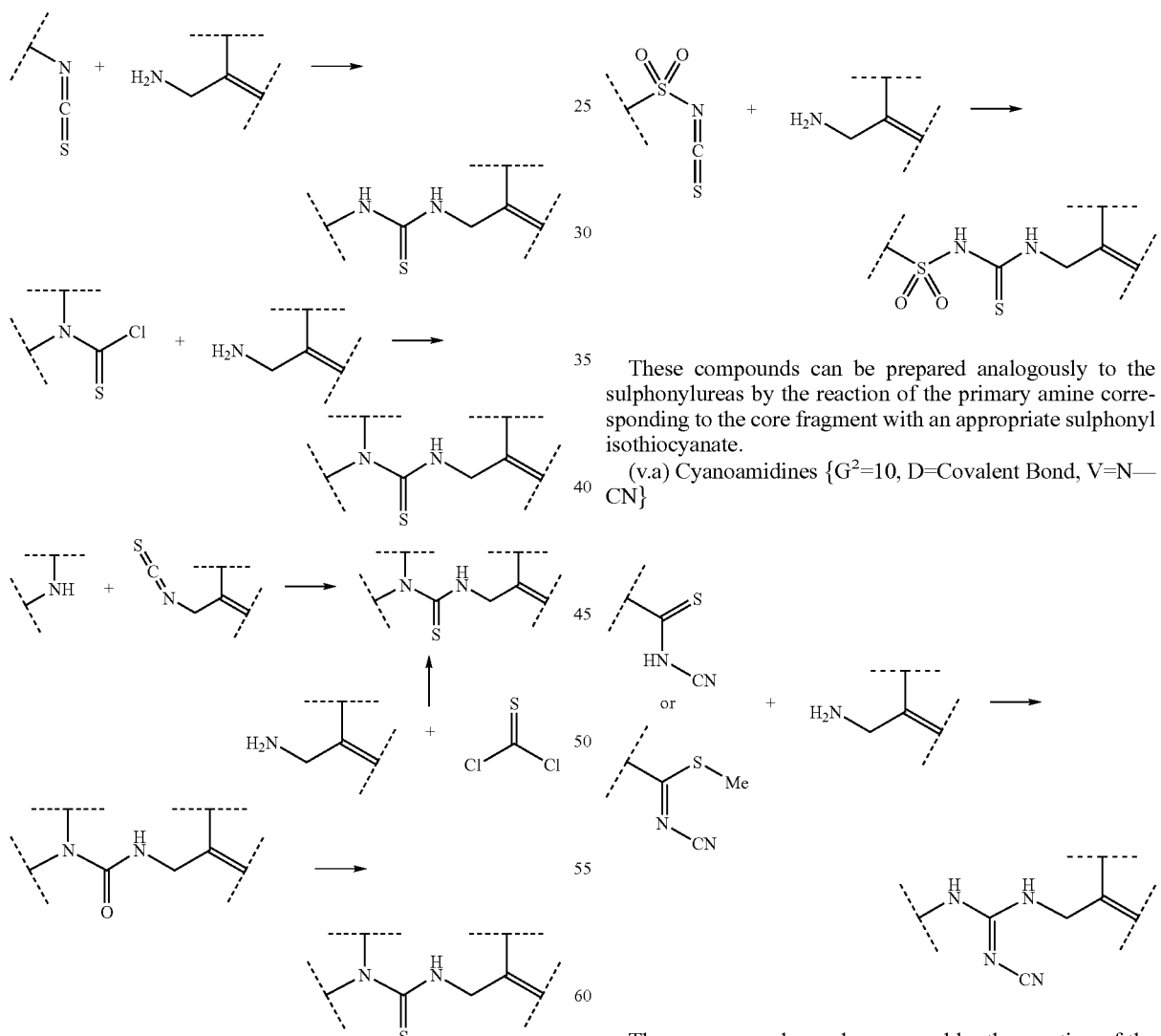

These compounds can be prepared by methods analogous to those described above for the ureas, simply by using the corresponding isothiocyanate and thiophosgene compounds.

(iv.a) Sulphonylureas {$G^2$=9, d=1, e=1, V=O}

These compounds can be prepared by the reaction of the primary amine corresponding to the core fragment with an appropriate sulphonyl isocyanate. The reaction conditions are similar to those described above for the reaction of an amine with an isocyanate to prepare the ureas.

(iv.b) Sulphonylthioureas {$G^2$=9, d=1, e=1, V=S}

These compounds can be prepared analogously to the sulphonylureas by the reaction of the primary amine corresponding to the core fragment with an appropriate sulphonyl isothiocyanate.

(v.a) Cyanoamidines {$G^2$=10, D=Covalent Bond, V=N—CN}

These compounds can be prepared by the reaction of the primary amine of the core fragment with an N-cyanothioamide or an N-cyanothioimidate corresponding to the $G^2$ fragment.

(v.b) Cyanoguanidines {$G^2$=9, d=Zero, e=1, V=N—CN; $G^2$=10, D=NH, V=N—CN; $G^2$=11, V=N—CN}

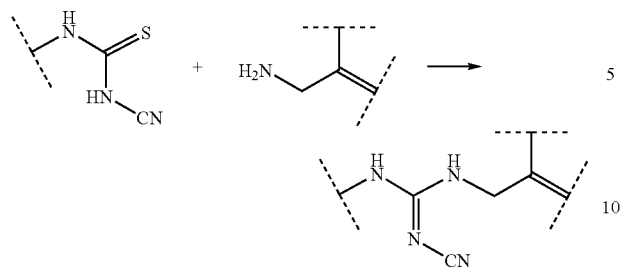

These compounds can be prepared by the reaction of the primary amine of the core fragment with a cyanothiourea corresponding to the $G^2$ fragment in the presence of a carbodiimide.

(v.c) Sulphonylcyanoguanidines $\{G^2=9, d=1, e=1, V=N-CN\}$

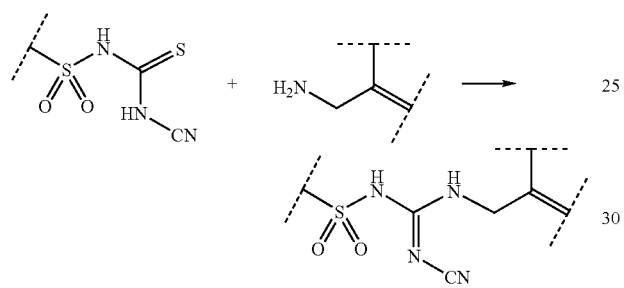

These compounds can be prepared in an analogous manner by the reaction of the primary amine of the core fragment with an N-sulphonyl-N'-cyanothiourea corresponding to the $G^2$ fragment in the presence of a carbodiimide.

The reagents corresponding to the fragments are commercially available, or they can be prepared by methods described in the literature. Particularly relevant leading references include the following.

Synthesis of Fused Azepine Derivatives for $G^1$:

Aranapakam et al., Bioorg. Med. Chem. Lett. 1993, 1733; Artico et al., Farmaco. Ed. Sci. 24, 1969, 276; Artico et al., Farmaco. Ed. Sci. 32, 1977, 339; Chakrabarti et al., J. Med. Chem. 23, 1980, 878; Chakrabarti et al., J. Med. Chem. 23, 1980, 884; Chakrabarti et al., J. Med. Chem. 32, 1989, 2573; Chimirri et al., Heterocycles 36, 1993, 601; Grunewald et al., J. Med. Chem. 39, 1996, 3539; Klunder et al., J. Med. Chem. 35, 1992, 1887; Liegéois et al., J. Med. Chem. 37, 1994, 519; Olagbemiro et al., J. Het. Chem. 19, 1982, 1501; Wright et al., J. Med. Chem. 23, 1980, 462; Yamamoto et al., Tet. Lett. 24, 1983, 4711; and International patent application, publication number WO99/06403.

Synthesis of Amidine Transfer Reagents for $G^2$, V=N—CN

Mestres et al., Synthesis, 1980, 755; Petersen et al., J. Med. Chem. 21, 1978, 773; and Cord, J. Chem. Soc., 1948, 1620.

Synthesis of Proline Derivatives for $G^2$=Group According to 11

Dugave et al., Tet. Lett. 39, 1998, 1169; Petrillo et al., J. Med. Chem. 31, 1988, 1148; and Smith et al., J. Med. Chem. 31, 1988, 875.

The foregoing general description is further illustrated below with a number of non-limiting examples.

EXAMPLES

Abbreviations
The following abbreviations have been used.

| | |
|---|---|
| AIBN | Azo-bis-(isobutyronitrile) |
| BOC | tert-Butyloxycarbonyl |
| $(BOC)_2O$ | Di-tert-butyl dicarbonate |
| DMF | Dimethylformamide |
| EtOAc | Ethyl acetate |
| IPA | Isopropanol |
| M.S. | Mass spectrometry |
| NBS | N-Bromosuccinimide |
| pet. ether | petroleum ether, fraction boiling at 60–80° C. |
| THF | Tetrahydrofuran |
| WSCDI | Water-soluble carbodiimide |

Preparation of Intermediates

Reagents corresponding to fragments $G^1$ and $G^2$ were commercially available or prepared according to the published procedures except where detailed in the specific Examples. Reagents corresponding to the core fragment were prepared as detailed below.

Example A 4-(tert-Butyloxycarbonylaminomethyl)-3-chlorobenzoic acid

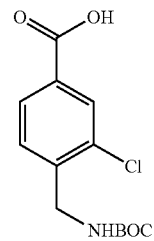

A1. Methyl 4-bromomethyl-3-chlorobenzoate

To a solution of methyl 3-chloro-4-methylbenzoate (5.0 g, 27.1 mmol) in carbon tetrachloride (50 ml) were added NBS (5.8 g, 32.0 mmol) and AIBN (0.442 g, 2.70 mmol). The mixture was stirred at reflux for 18 h. The mixture was allowed to cool to room temperature and then concentrated in vacuo. The residue was purified by flash chromatography on silica (eluant EtOAc:pet. ether 0:100 to 5:95); yield 5.96 g (84%).

A2. 4-(tert-Butyloxycarbonylaminomethyl)-3-chlorobenzoic acid

To a saturated solution of ammonia in ethanol (170 ml) was added methyl 4-bromomethyl-3-chlorobenzoate from Example A1 (5.5 g, 20.9 mmol). The mixture was stirred at room temperature for 1 hr and then concentrated in vacuo. The residue was triturated with diethyl ether and the resultant white crystals were filtered off and washed with more diethyl ether. To a solution of this solid in water (100 ml)

were added solutions of (BOC)₂O (5.0 g, 23.0 mmol) in dioxan (100 ml) and sodium hydroxide (1.86 g, 46.0 mmol) in water (100 ml). The mixture was stirred at room temperature for 18 h and then concentrated in vacuo. The aqueous residue was acidified with citric acid and extracted with chloroform/IPA. The organic layer was washed with water, dried over MgSO₄, and concentrated in vacuo to give a white solid; yield 2.8 g (67%).

Example B 4-(tert-Butyloxycarbonylaminomethyl)-3-nitrobenzoic acid

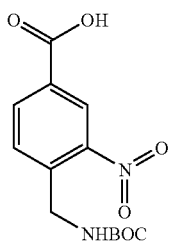

4-Bromomethyl-3-nitrobenzoic acid (4.75 g, 18.2 mmol) was reacted following the method of Example A2 to give a yellow solid; yield 2.6 g (49%).

Example C

4Cyano-3methylbenzoic acid

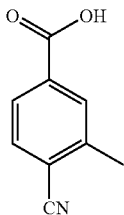

To a solution of 4bromo-2-methylbenzonitrile (2.0 g, 10.2 mmol) in THF (100 ml) at −78° C. under a nitrogen atmosphere was added dropwise a 2.5M solution of n-butyl lithium (4.48 ml, 11.2 mmol). The mixture was stirred at −78° C. for 1 h and then poured onto solid carbon dioxide (5 g) in THF (50 ml). The mixture was allowed to warm to room temperature. Water was added (200 ml) and the mixture was extracted with diethyl ether (3 times). The aqueous layer was acidified by addition of concentrated HCl and extracted with chloroform (3 times). The combined chloroform extracts were washed with water, dried over MgSO₄, and concentrated in vacuo to give a white solid; yield 1.2 g (73%).

Example D

4-Cyano-2-methylbenzoic acid

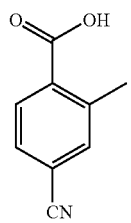

4Bromo-3methylbenzonitrile (2.0 g, 10.2 mmol) was reacted following the method of Example C to give a yellow solid which was triturated with hexane and filtered off; yield 0.96 g (59%).

Example E 4-(tert-Butyloxycarbonylaminomethyl)-2-fluorobenzoic acid

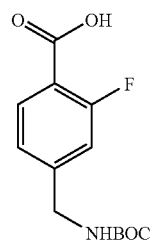

E1. 2-Fluoro-4-methylbenzoic acid

4-Bromo-3-fluorotoluene (8.33 g, 44.07 mmol) was reacted following the method of Example C to give a white solid; 4.89 g (72%).

E2. Methyl 2-fluoro-4-methylbenzoate

To a solution of 2-fluoro-4-methylbenzoic acid from Example E1 (6.04 g, 39.18 mmol) in toluene (80 ml) was added thionyl chloride (65 ml, 89.11 mmol). The mixture was heated at reflux for 2.5 h, cooled and concentrated in vacuo. The residue was dissolved in dichloromethane (50 ml) and methanol (50 ml) was added. The mixture was stirred at room temperature for 2.5 h and then concentrated in vacuo. The residue was dissolved in dichloromethane (100 ml), washed with saturated sodium bicarbonate solution and brine, dried over MgSO₄, and concentrated in vacuo to give a tan solid; yield 5.07 g (77%).

E3. Methyl 4-bromomethyl-2-fluorobenzoate

Methyl 2-fluoro-4-methylbenzoate from Example E2 (5.07 g, 30.16 mmol) was reacted following the method of Example of A1. The product was purified by flash chromatography on silica (eluant EtOAc:pet. ether 20:80); yield 5.9 g (80%).

E4. 4(tert-Butyloxycarbonylaminomethyl)-2-fluorobenzoic acid

Methyl 4-bromomethyl-2-fluorobenzoate from Example E3 (5.9 g, 24.13 mmol) was reacted following the method of Example A2. The product was recrystallised from dioxan/pet. ether to give white crystals; yield 2.46 g (38%).

Example F 6-(tert-Butyloxycarbonylaminomethyl)-2-chloronicotinic acid

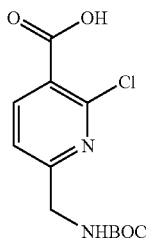

F1. Methyl 2-chloro-6-methylnicotinate

To a suspension of 2-chloro-6-methylnicotinic acid (5.3 g, 30.8 mmol) in dichloromethane (100 ml) at 0° C. were added DMF (1 ml) and oxalyl chloride (3.2 ml, 36.9 mmol). The mixture was allowed to warmn to room temperature and stirred for 5 h. The solvents were removed in vacuo and the residue was dissolved in dichloromethane (50 ml) and methanol (50 ml). The mixture was stirred at room temperature for 18 h and then concentrated in vacuo. The residue was dissolved in chloroform, washed with saturated sodium bicarbonate solution and brine, dried over MgSO$_4$, and concentrated in vacuo to give a brown oil; yield 5.70 g (100%).

F2. Methyl 6-bromomethyl-2-chloronicotinate

Methyl 2-chloro-6-methyinicofinate from Example F1 (5.70 g, 30.8 mmol) was reacted following the method of Example of A1. The product was purified by flash chromatography on silica (eluant EtOAC:pet. ether 20:80); yield 4.8 g (58%).

F3. Methyl 6-(tert-butyloxycarbonylaminomethyl)-2-chloronicotinate

Methyl 6-bromomethyl-2-chloronicotinate from Example F2 (4.8 g, 18.0 mmol) was reacted following the method of Example of A2 to give an off white solid; yield 1.45 g (28%).

Example G 6-(tert-Butyloxycarbonylaminomethyl)nicotinic acid

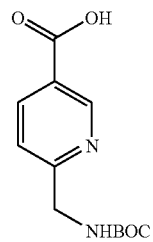

G1. Methyl 6-(bromomethyl)nicotinate

Methyl 6-methyinicotinate (5.0 g, 33.0 mmol) was reacted following the method of Example A1. The product was purified by flash chromatography on silica (eluant EtOAc:pet. ether 20:80); yield 3.7 g (49%).

G2. Methyl 6-(azidomethyl)nicotinate

To a solution of methyl 6-(bromomethyl)nicotinate from Example G1 (2.0 g, 8.60 mmol) in DMF (15 ml) was added sodium azide (0.84 g, 12.9 mmol). The mixture was stirred at room temperature for 18 h. EtOAc (100 ml) was added and the mixture was washed with water (3 times), dried over MgSO$_4$, and concentrated in vacuo. The residue was purified by flash chromatography on silica (eluant EtOAc:pet ether 20:80) to give a yellow gum; yield 1.55 g (93%).

G3. Methyl 6-(tert-butyloxycarbonylaminomethyl)nicotinate

To a degassed solution of methyl 6-(azidomethyl)nicotinate from Example G2 (1.6 g, 8.30 mmol) in methanol (50 ml) was added 10% palladium-on-carbon (0.15 g). Hydrogen gas was bubbled through the mixture for 2 h at room temperature. The catalyst was removed by filtration through a pad of celite and the filtrate was evaporated in vacuo. The residue was dissolved in dichloromethane and cooled to 0° C. To this solution were added triethylamine (1.67 g, 16.0 mmol) and (BOC)$_2$O (2.17 g, 9.96 mmol). The mixture was allowed to warm to room temperature and stirred for 18 h, then concentrated in vacuo. The residue was dissolved in EtOAc and washed with water, dried over MgSO$_4$, and concentrated in vacuo. The residue was purified by flash chromatography on silica (eluant EtOAc:pet. ether 50:50) to give a yellow solid; yield 1.57 g (71%).

G4. 6-(tert-Butyloxycarbonylaminomethyl)nicotinic acid

To a solution of methyl 6-(tert-butyloxycarbonylaminomethyl)nicotinate from Example G3 (1.56 g, 5.84 mmol) in THF (20 ml) and water (5 ml) was added lithium hydroxide monohydrate (0.37 g, 8.76 mmol). The mixture was stirred at room temperature for 18 h and then concentrated in vacuo. The aqueous residue was acidified by addition of 1M citric acid solution and extracted with chloroform/IPA (3 times). The combined organic extracts were washed with brine, dried over MgSO$_4$, and evaporated in vacuo to give a white solid; yield 1.38 g (94%).

Example H

4/5-Bromo-6-(tert-butyloxycarbonylaminomethyl)-1-methyl)-2-oxo-1,2-dihydropyridine-3-carboxylic acid

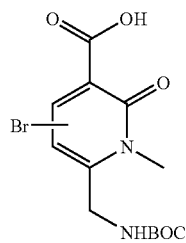

H1. Methyl 1,6-dimethyl-2-oxo-1,2-dihydropyridine-3-carboxylate

To a solution of 3-hydroxy-6-methyinicotinic acid (10 g, 65.0 mmol) in DMF (100 ml) at 0° C. was added sodium hydride (4.83 g, 60% dispersion, 140 mmol). The mixture was stirred at 0° C. for 1.5 h, then methyl iodide (12.4 ml, 195 mmol) was added and the mixture was allowed to warm to room temperature, stirring for a further 18 h. The mixture was partitioned between water and EtOAc and the aqueous layer acidified to pH 5. The layers were separated and the organic layer was washed with brine, dried over MgSO₄, and concentrated in vacuo. The residue was purified by flash chromatography on silica (eluant dichloromethane/methanol 95:5) to give a white solid. This was recrystallised from methanol and the filtrate was evaporated in vacuo to give the desired product; yield 6.1 g (52%).

H2. Methyl 4/5-bromo-6-bromomethyl-methyl-2-oxo-1,2-dihydropyridine-3-carboxylate Methyl 1,6-dimethyl-2-oxo-1,2-dihydropyridine-3-carboxylate of Example H1 (6.0 g, 33.0 mmol) was reacted following the method of Example of A1. The product was purified by flash chromatography on silica (eluant dichloromethane/methanol 95:5); yield 5.2 g (46%).

H3. 4/5-Bromo-6-(tert-butyloxycarbonylaminomethyl)-1-methyl-2-oxo-1,2-dihydropyridine-3-carboxylic acid Methyl 4/5-bromo-6-bromomethyl-1-methyl-2-oxo-1,2dihydropyridine-3-carboxylate of Example H2 (5.2 g, 14.8 mmol) was reacted following the method of Example A2 to give a brown gum; yield 1.3 g (24%).

Example I

4-Cyano-3,5-dimethylbenzoic acid

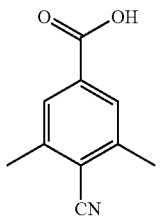

I1. 4-Bromo-2,6-dimethylbenzonitrile

4-Bromo-2,6dimethylaniline (4.49 g, 22.4 mmol) was taken up in water (25 ml) and concentrated hydrochloric acid (8.0 ml) was added. The mixture was sonicated to form a fine suspension and then cooled to 0° C. A solution of sodium nitrite (1.67 g, 24.2 mmol) in water (5 ml) was then added dropwise so as to maintain the temperature of the reaction between 0–5° C. The mixture was stirred at 0–5° C. for ½ h and then neutralised by addition of solid sodium carbonate. The resulting solution was then added portionwise to a solution of copper cyanide (2.42 g, 27.0 mmol) and potassium cyanide (3.65 g, 56.1 mmol) in water (25 ml) at 70° C. The mixture was stirred at 70° C. for ½ h, allowed to cool and then extracted with toluene (2 times). The combined extracts were washed with water and brine, dried over MgSO₄, and concentrated in vacuo. The residue was purified by flash chromatography on silica (eluant EtOAc: pet. ether 5:95) to give an orange solid; yield 3.2 g (68%).

I2. 4-Cyano-3,5-dimethylbenzoic acid

4-Bromo-2,6-dimethylbenzonitrile from Example I1 (3.20 g, 15.2 mmol) was reacted following the method of Example C to give a tan solid; yield 1.5 g (56%).

Reagents corresponding to fragments A, B and C were combined to give the specific Examples as detailed below.

Example 1

1-(4-[3-(2,6-Difluorophenyl)ureidomethyl]benzoyl)-2,3,4,5-tetrahydro-1H-1-benzazepine

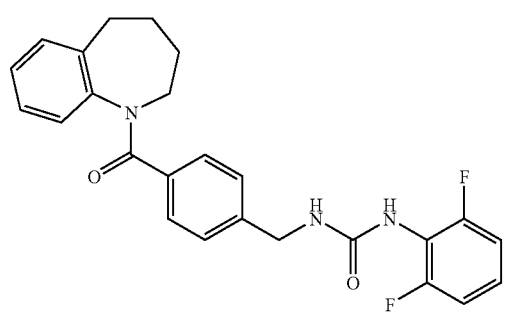

1A. 1-(4-Cyanobenzoyl)-2.3,4,5-tetrahydro-1H-1-benzazepine

To a solution of 2,3,4,5-tetrahydro-1H-1-benzazepine (1.05 g, 7.14 mmol) in dichloromethans (40 ml) were added 4-cyanobenzoic acid (1.26 g, 8.57 mmol), triethylamine (1.00 g, 7.14 mmol), 4-(dimethylamino)pyridine (0.87 g, 7.14 mmol) and WSCDI (2.86 g, 14.28 mmol). The mixture was stirred at reflux for 18 h, cooled and evaporated in vacuo. The residue was partitioned between EtOAc and 1M $KHSO_4$. The organic layer was washed with saturated sodium bicarbonate solution and brine, dried over $MgSO_4$, and concentrated in vacuo to give a white solid; yield 1.50 g (76%).

1B. 1-(4-(Aminomethyl)benzoyl)-2,3,4,5-tetrahydro-1H-1-benzazepine

To a degassed solution of the cyanobenzoyl benzaz pin from Example 1A (1.50 g, 5.43 mmol) in methanol (50 ml) were added concentrated hydrochloric acid (1.4 ml, 16.2 mmol) and 10% palladium-on-carbon (1.15 g). Hydrogen gas was bubbled through the mixture for 5 h at room temperature. The catalyst was removed by filtration through a pad of celite and the filtrate was evaporated in vacuo. The residue was partitioned between EtOAc and water. The aqueous layer was basified by addition of saturated sodium bicarbonate solution and extracted with dichloromethane (2 times). The combined organic extracts were washed with brine, dried over $MgSO_4$, and concentrated in vacuo to give a white solid; yield 1.12 g (74%).

1C. 1-(4-[3-(2,6-Difluorophenyl)ureidomethyl]benzoyl)-2,3,4,5-tetrahydro-1H-1-benzazepine To a solution of the amine from Example 1B (0.50 g, 1.79 mmol) in dichloromethane (20 ml) were added triethylamine (0.27 ml, 1.97 mmol) and 2,6-difluorophenylisocyanate (0.31 g, 1.97 mmol). The mixture was stirred at room temperature for 2 h and then evaporated in vacuo. The residue was purfiied by flash chromatography on silica (eluant EtOAc:pet. ether 50:50) to give a white solid; yield 0.62 g (80%).

M.S.: calc m/e=435.18. found [M+H]$^+$=436.

Example 2

1-(4-[3-(2,6-Difluorophenyl)cyanoguanidinomethyl]benzoyl)-2,3,4,5-tetrahydro-1H-1-benzazepine

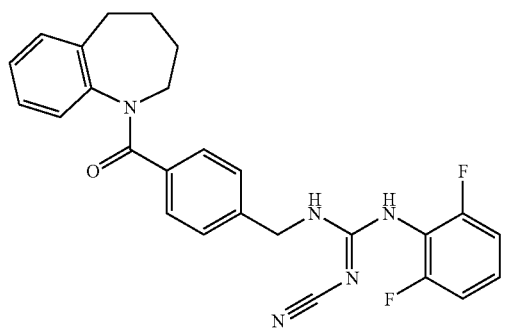

To a solution of the amine from Example 1B (0.12 g, 0.379 mmol) in DMF (20 ml) were added 1-(2,6-difluorophenyl)-3-cyano-thiourea (0.16 g, 0.758 mmol, prepared according to Atwal et. al., Tetrahedron Lett., 30, p7313, 1989.), diisopropylethylamine (0.16 ml, 0.947 mmol) and WSCDI (0.0879, 0.455 mmol). The mixture was stirred at room temperature for 72 h and then evaporated in vacuo. The residue was partitioned between dichloromethane and 1M $KHSO_4$. The organic layer was washed with saturated sodium bicarbonate solution and brine, dried over $MgSO_4$ and concentrated in vacuao. The residue was purified by flash chromatography on silica (eluant EtOAc:pet. ether 50:50–70:30) to give a white solid; yield 0.084 g (48%).

M.S.: calc m/e=459.19. found [M+H]$^+$=460.0

Example 3

1-(6-[3-(2,6-Difluorophenyl)ureidomethyl]nicotinoyl)-2,3,4,5-tetrahydro-1H-1-benzazepine

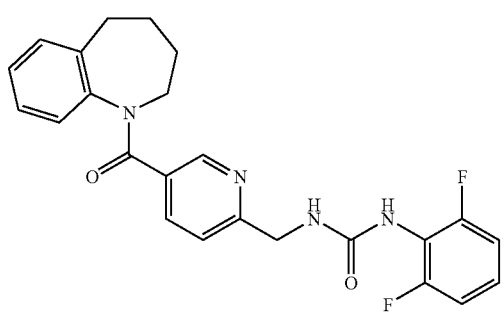

3A. 1-[6-(tert-Butyloxycarbonylaminomethyl)nicotinoyl]-2,3,4,5-tetrahydro-1H-1-benzazepine The carboxylic acid from Example G4 (1.38 g, 5.45 mmol) was reacted with 2,3,4,5-tetrahydro-1H-1-benzazepine (0.80 g, 5.50 mmol) according to the procedure in Example 1A. The product was purified by flash chromatography on silica (eluant EtOAc:pet. ether 30:70-70:30); yield 1.14 g (55%).

3B. 1-[6-(Aminomethyl)nicotinoyl]-2,3,4,5-tetrahydro-1H-1-benzazepine hydrochloride The BOC amine from Example 3A (1.14 g, 2.98 mmol) was dissolved in 4N HCl/dioxan, stirred at room temperature for 1 h and then evaporated in vacuo, azeotroping with toluene, to give an off white solid; yield 1.0 g (quantitative).

3C. 1-(6-[3-(2,6-Difluorophenyl)ureidomethyl]nicotinoyl)-2,3,4,5-tetrahydro-1H-1-benzazepine The amine hydrochloride from Example 3B (0.070 g, 0.220 mmol) was reacted with 2,6-difluorophenylisocyanate (0.038 g, 0.242 mmol) according to the procedure in Example 1C. Th product was purified by trituration with diethyl ether to give a white solid; yield 0.060 g (63%).

M.S.: calc m/e=436.47. found [M+H]$^+$=437.2.

Example 4

1-(3-Chloro-4-[3-(3-methoxyphenyl)ureidomethyl]benzoyl)-2,3,4,5-tetrahydro-1H-1-benzazepine

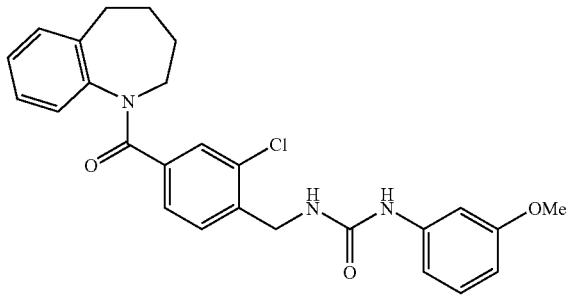

4A. 1-(4-[tert-Butyloxycarbonylaminomethyl]-3-chlorobenzoyl)-2,3,4,5-tetrahydro-1H-1-benzazepine The carboxylic acid from Example A2 (1.0 g, 3.50 mmol) was reacted with 2,3,4,5-tetrahydro-1H-1-benzazepine (0.47 g, 3.20 mmol) according to the procedure in Example 1A. The product was purified by flash chromatography on silica (eluant EtOAc:pet. ether 30:70–40:60); yield 0.88 g (66%).

4B. 1-(4-[Aminomethyl]-3-chlorobenzoyl)-2,3,4,5-tetrahydro-1H-1-benzazepine hydrochloride The BOC amine from Example 4A (0.88 g, 2.10 mmol) was dissolved in 4N HCl/dioxan and stirred at room temperature for 1 h, then evaporated in vacuo, azeotroping with toluene, to give a white solid; yield 0.70 g (95%).

4C. 1-(3-Chloro-4-[3-(3-methoxyphenyl)ureidomethyl]benzoyl)-2,3,4,5-tetrahydro-1H-1-benzazepine The amine hydrochloride from Example 4B (0.050 g, 0.140 mmol) was reacted with 3-methoxyphenylisocyanate (0.021 g, 0.140 mmol) according to the procedure in Example 1C. The product was purified by trituration with diethyl ether to give a white solid; yield 0.060 g (93%).

M.S.: calc m/e=463.17. found [M+H]$^+$=464.2.

Example 5

1-(3-Chloro-4-[3-(2-chloropheny)ureidomethyl]benzoyl)-2,3,4,5-tetrahydro-1H-1-benzazepine

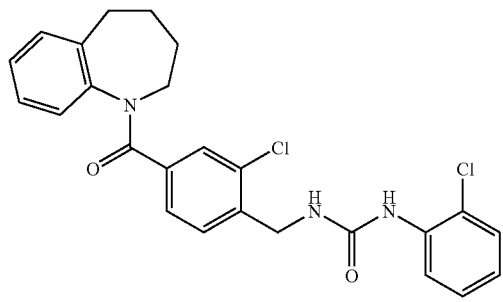

The amine hydrochloride from Example 4B (0.050 g, 0.140 mmol) was reacted with 2-chlorophenylisocyanate (0.022 g, 0.140 mmol) according to the procedure in Example 1C. The product was purified by trituration with diethyl ether to give a white solid; yield 0.063 g (98%).

M.S.: calc m/e=467.12. found [M+H]$^+$; $^{35}$Cl=468.1.

Example 6

1-(3-Chloro-4-[3-(2,6-difluorophenyl)thioureidomethyl]benzoyl)-2,3,4,5-tetrahydro-1H-1-benzazepine

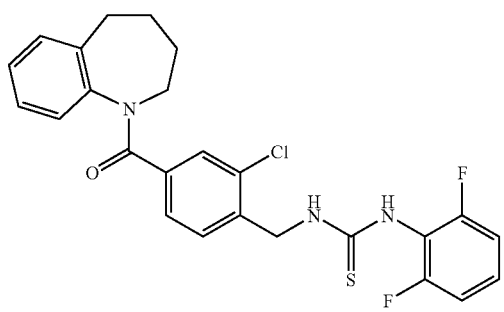

The amine hydrochloride from Example 4B (0.075 g, 0.214 mmol) was reacted with 2,6-difluorophenylisocyanate (0.054 g, 0.320 mmol) according to the procedure in Example 1C. The product was purified by flash chromatography on silica (eluant EtOAc:pet. ether 30:70-45:55); yield 0.068 g (66%).

M.S.: calc m/e=485.11. found [M+H]$^+$; $^{35}$Cl=486.2, [M+H]$^+$; $^{37}$Cl=488.1

Example 7

1-(4-[3-(2,6-Difluorophenyl)ureidomethyl]-2-methylbenzoyl)-2,3,4,5-tetrahydro-1H-1-benzazepine

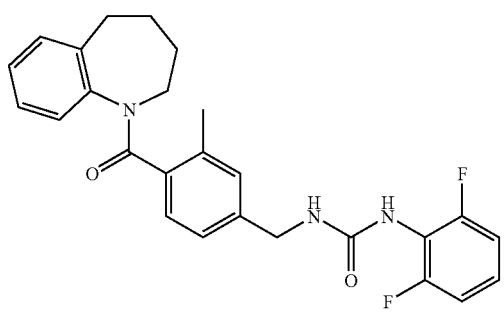

7A. 1-(4-Cyano-2-methylbenzoyl)-2,3,4,5-tetrahydro-1H-1-benzazepine

The carboxylic acid from Example D (0.96 g, 5.95 mmol) was reacted with 2,3,4,5-tetrahydro-1H-1-benzazepine (0.80 g, 5.44 mmol) according to the procedure in Example 1A. The product was purified by flash chromatography on silica (eluant EtOAc:pet. ether 30:70); yield 0.59 g (38%).

7B. 1-(4-[Aminomethyl]-2-methylbenzoyl)-2,3,4,5-tetrahydro-1H-1-benzazepine hydrochloride The cyanobenzoyl benzazepine from Example 7A (0.59 g, 2.03 mmol) was hydrogenated according to the procedure in Example 1B. The product was isolated as the HCl salt; yield 0.55 g (82%).

7C. 1-(4-[3-(2,6-Difluorophenyl)ureidomethyl]-2-methylbenzoyl)-2,3,4,5-tetrahydro-1H-1-benzazepine The amine hydrochloride from Example 7B (0.050 g, 0.151 mmol) was reacted with 2,6difluorophenylisocyanate (0.028 g, 0.181 mmol) according to the procedure in Example 1C. The product was purified by flash chromatography on silica (eluant EtOAc:pet. ether 50:50); yield 0.041 g (62%).

M.S.: calc m/e=449.19. found [M+H]$^+$=450.1.

Example 8

1-(3-Methyl-4-[3-(phenylsulfonyl)ureidomethyl]benzoyl)-2,3,4,5-tetrahydro-1H-1-benzazepine

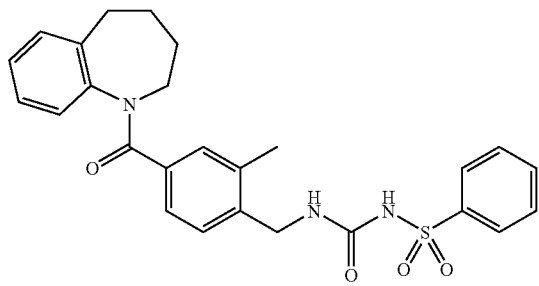

8A. 1-(4-Cyano-3-methylbenzoyl)-2,3,4,5-tetrahydro-1H-1-benzazepine

The carboxylic acid from Example C (0.96 g, 5.95 mmol) was reacted with 2,3,4,5-tetrahydro-1H-1-benzazepine (0.80 g, 5.44 mmol) according to the procedure in Example 1A. The product was purified by flash chromatography on silica (eluant EtOAc:pet. ether 30:70); yield 1.10 g (70%).

8B. 1-(4-[Aminomethyl]-3-methylbenzoyl)-2,3,4,5-tetrahydro-1H-1-benzazepine hydrochloride The cyanobenzoyl benzazepine from Example 8A (1.10 g, 3.79 mmol) was hydrogenated according to the procedure in Example 1B. The product was isolated as the HCl salt; yield 1.23 g (98%).

8C. 1-(3-Methyl-4-[3-(Phenylsufonyl)ureidomethyl]benzoyl)-2,3,4,5-tetrahydro-1H-1-benzazepine The amine hydrochloride from Example 8B (0.050 g, 0.151 mmol) was reacted with phenylsulphonylisocyanate (0.028 g, 0.151 mmol) according to the procedure in Example 1C. The product was purified by flash chromatography on silica (eluant EtOAc:pet. ether 80:20); yield 0.026 g (22%).

M.S.: calc m/e=477.17. found [M+H]$^+$=478.2.

Example 9

1-(3-Methyl-4-[3-(2-oxo-1,2-dihydropyrid-3-yl)ureidomethyl]benzoyl)-2,3,4,5-tetrahydro-1H-1-benzazepine

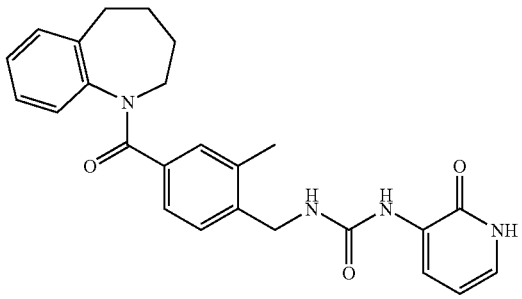

To a suspension of 2-hydroxynicotinic acid (95 mg, 0.68 mmol) in dioxan (5 ml) were added triethylamine (0.11 ml, 0.771 mmol) and diphenylphosphoryl azide (0.16 ml, 0.725 mmol). The mixture was stirred at reflux for 3 h. The amine hydrochloride from Example 8B (0.15 g, 0.453 mmol) and triethylamine (0.095 ml, 0.680 mmol) were added and the mixture was stirred at reflux for a further 18 h, cooled and evaporated in vacuo. The residue was partitioned between dichloromethane and 1 M KHSO$_4$. The organic layer was washed with saturated sodium bicarbonate solution and brine, dried over MgSO$_4$, and concentrated in vacuo. The residue was purified by flash chromatography on silica (eluant methanol:dichloromethane 2:98–5:95) to give a white solid; yield 0.084 g (43%). M.S.: calc m/e=430.20. found [M+H]$^+$=431.1.

Example 10

1-(4-[3-(2,6-Difluorophenyl)ureidomethyl]-3-methylbenzyl)-2,3,4,5-tetrahydro-1H-1-benzazepine

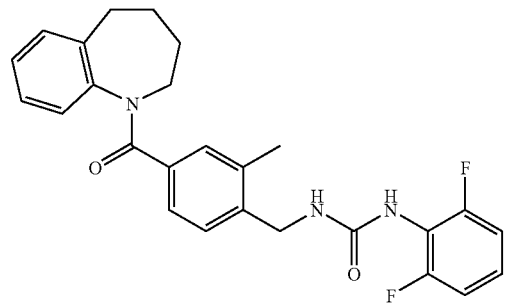

The amine hydrochloride from Example 8B (0.050 g, 0.151 mmol) was reacted with 2,6-difluorophenylisocyanate (0.028 g, 0.181 mmol) according to the procedure in Example 1C. The product was purified by flash chromatography on silica (eluant EtOAc:pet. ether 50:50); yield 0.044 g (65%).

M.S.: calc m/e=449.19. found [M+H]$^+$=450.1.

Example 11

1-(3-Nitro-4-[2-nitrobenyzlsulfonylaminomethyl]
benzoyl)-2,3,4,5-tetrahydro-1H-1-benzazepine

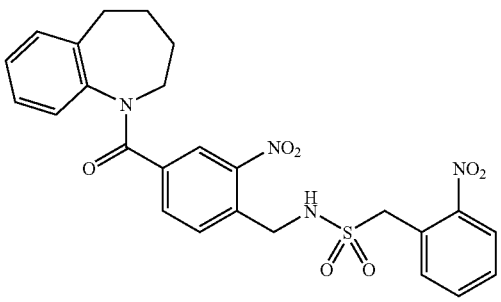

11A. 1-(4-[tert-Butyloxycarbonylaminomethyl]-3-nitrobenzoyl)-2,3,4,5-tetrahydro-1H-1-benzazepine The carboxylic acid from Example B (0.911 g, 3.08 mmol) was reacted with 2,3,4,5-tetrahydro-1H-1-benzazepine (0.453 g, 3.08 mmol) according to the procedure in Example 1A. The product was purified by flash chromatography on silica (eluant EtOAc:pet. ether 50:50); yield 0.58 g (43%).

11B. 1-(4-[Aminomethyl]-3-nitrobenzoyl)-2,3,4,5-tetrahydro-1H-1-benzazepine hydrochloride The BOC-aminomethylbenzoyl benzazepine from Example 11A (0.33 g, 0.764 mmol) was reacted according to the procedure in Example 4B. The product was isolated as the HCl salt; yield 0.27 g (98%).

11C. 1-(3-Nitro-4-[2-nitrobenyzlsulfonylaminomethyl]benzoyl)-2,3,4,5-tetrahydro-1H-1-benzazepine The amine hydrochloride from Example 11B (0.068 g, 0.188 mmol) was reacted with 2-nitrobenzylsulphonyl chloride (0.033 g, 0.226 mmol) according to the procedure in Example 1C. The product was purified by flash chromatography on silica (eluant EtOAc:pet. ether 25:75-50:50); yield 0.010 g (10%).

M.S.: calc m/e=524.14. found [M+H]⁺=525.2.

Example 12

1-(3-Amino-4-[3-(2,6 difluorophenyl)ureidomethyl]
benzoyl)-2,3,4,5-tetrahydro-1H-1-benzazepine

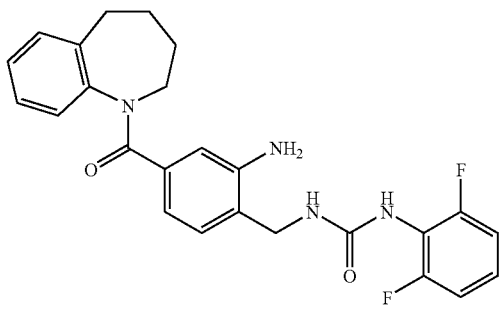

12A. 1-(3Amino-4-[tert-butyloxecarbonylaminomethyl]benzoyl)-2,3,4,5-tetrahydro-1H-1-benzazepine To a degassed solution of the nitrobenzoyl benzazepine from Example 11A (0.30 g, 0.700 mmol) in methanol (50 ml) was added 10% palladium-on-carbon (0.10 g). Hydrogen gas was bubbled through the mixture for 1.5 h at room temperature. The catalyst was removed by filtration through a pad of celite and the filtrate was evaporated in vacuo; yield 0.254 g (92%).

12B. 1-(3-Amino-4-[aminomethyl]benzoyl)-2,3,4,5-tetrahydro-1H-1-benzazepine dihydrochloride The BOC-aminomethylbenzoyl benzazepine from Example 12A (0.14 g, 0.354 mmol) was reacted according to the procedure in Example 4B. The product was isolated as the diHCl salt; yield 0.098 g (75%).

12C. 1-(3-Amino-4-[3-(2,6-difluorophenyl)ureidomethyl]benzoyl)-2,3,4,5-tetrahydro-1H-1-benzazepine The amine hydrochloride from. Example 12B (0.132 g, 0.35 mmol) was reacted with 2,6-difluorophenylisocyanate (0.055 g, 0.35 mmol) according to the procedure in Example 1C. The product was purified by flash chromatography on silica (eluant EtOAc:pet. eth r 70:30) and then by preparative HPLC (gradient water:acetonitrile 80:20–20:80; 0.1% TFA). The HPLC fractions were freeze-dried to give a white solid; yield 0.027 g (17%).

M.S.: calc m/e=450.19. found [M+H]⁺=451,2.

Example 13

1-(4-[3-(2,6-Difluorophenyl)ureidomethyl]-3-dimethylaminobenzoyl)-2,3,4,5-tetrahydro-1H-1-benzazepine

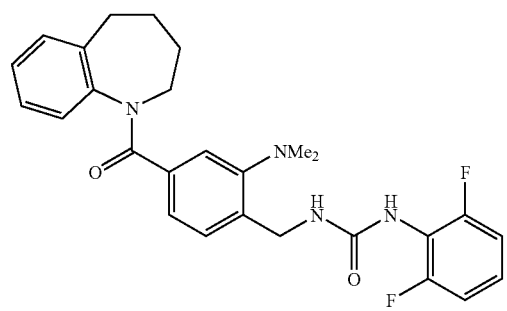

13A. 1-(4-[tert-Butyloxycarbonylaminomethyl]-3-dimethylaminobenzoyl)-2,3,4,5-tetrahydro-1H-1-benzazepine To an ice cold solution of the amine from Example 12A (0.16 g, 0.40 mmol) in 1% acetic acid/methanol (25 ml) was added formaldehyde (37% solution in water, 0.050 ml, 0.60 mmol). The mixture was stirred at 0° C. for 10 min and then sodium borohydride (0.050 g, 0.80 mmol) was added. The mixture was allowed to warm to room temperature with stirring over 1 h. and then evaporated in vacuo. The residue was partitioned between EtOAc and saturated sodium bicarbonate solution. The organic layer was washed with brine, dried over MgSO₄, and concentrated in vacuo. The residue was purified by flash chromatography on silica (eluant EtOAc:pet. ether 30:70–70:30) to give a white solid; yield 0.091 g (56%).

13B. 1-(4-[Aminomethyl]-3-dimethylaminobenzoyl)-2,3,4,5-tetrahydro-1H-1-benzazepine The BOC-aminomethylbenzoyl benzazepine from Example 13A (0.089 g, 0.225 mmol) was reacted according to the procedure in Example 4B. The product was isolated as the HCl salt; yield 0.075 g (97%).

13C. 1-(4-[3-(2,6-Difluorophenyl)ureidomethyl]-3-dimethylaminobenzoyl)-2,3,4,5-tetrahydro-1H-1-benzazepine The amine hydrochloride from Example 13B (0.075 g, 0.20 mmol) was reacted with 2,6-difluorophenylisocyanate (0.032 g, 0.20 mmol) according to the procedure in Example 1C. The product was purified by flash chromatography on silica (eluant EtOAc:pet. ether 90:10); yield 0.044 g (65%).
M.S.: calc m/e=478.22. found [M+H]⁺=479.2.

Example 14

1-(4-[3-(2,6-Difluorophenyl)ureidomethyl]-2-fluorobenzoyl)-2,3,4,5-tetrahydro-1H-1-benzazepine

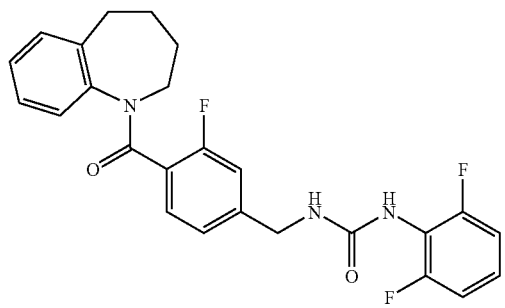

14A. 1-(4-[tert-Butyloxycarbonylaminomethyl]-2-fluorobenzoyl)-2,3,4,5-tetrahydro-1H-1-benzazepine The carboxylic acid from Example E4 (0.60 g, 2.22 mmol) was reacted with 2,3,4,5-tetrahydro-1H-1-benzazepin (0.289, 1.89 mmol) according to the procedure in Example 1A. The product was purified by flash chromatography on silica (eluant EtOAc:pet. ether 40:60); yield 0.58 g (77%).

14B. 1-(4-[Aminomethyl]-2-fluorobenzoyl)-2,3,4,5-tetrahydro-1H-1-benzazepine The BOC-aminomethylbenzoyl benzazepine from Example 14A (0.58 g, 1.42 mmol) was reacted according to the procedure in Example 4B. The product was isolated as the HCl salt; yield 0.29 g (60%).

14C. 1-(4-[3-(2,6-Difluorophenyl)ureidomethy]-2-fluorobenzoyl)-2,3,4,5-tetrahydro-1H-1-benzazepine The amine hydrochloride from Example 14B (0.040 g, 0.12 mmol) was reacted with 2,6-difluorophenylisocyanate (0.020 g, 0.13 mmol) according to the procedure in Example 1C. The product was purified by flash chromatography on silica (eluant EtOAc:pet. ether 40:60–100:0); yield 0.038 g (70%).
M.S.: calc m/e=453.17. found [M+H]⁺=454.1.

Example 15

1-(4-[3-(2,6-Difluorophenyl)ureidomethyl]-3-methylbenzoyl)-2,3,4,5-tetrahydro-1H-1,5-bezazepine

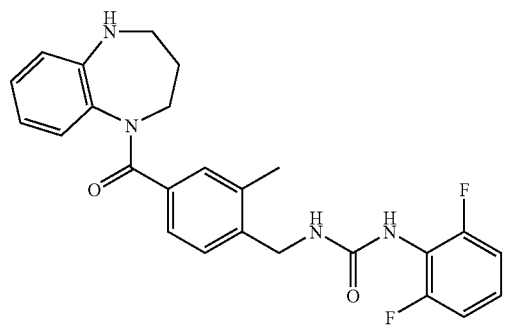

15A. 2,3,4,5-Tetrahydro-1H-1,5-benzodiazepine

To an ice cold solution of lithium aluminium hydride (4.68 g, 123 mmol) in dry THF (100 ml), under a nitrogen atmosphere, was added dropwise a solution of 2,3,4,5-tetrahydro-1H-1,5-benzodiazepin-2-one (5.0 g, 30.9 mmol) in dry THF (50 ml). The mixture was allowed to warm to room temperature and then heated at reflux for 2 h. The mixture was then cooled to 0° C. and a solution of aqueous ammonium hydroxide (10 ml) in THF (60 ml) was added dropwise. The resultant suspension was stirred for 1 h and then filtered through a pad of celite. The filtrate was evaporated in vacuo to give a tan solid; yield 4.36 g (95%).

15B. 1-(4-Cyano-3-methylbenzoyl)-2,3,4,5-tetrahydro-1H-1,5-benzodiazepine

The carboxylic acid from Example C (0.65 g, 4.03 mmol) was reacted with 2,3,4,5-tetrahydro-1H-1,5-benzodiazepine from Example 15A (0.50 g, 3.36 mmol) according to the procedure in Example 1A. The product was purified by flash chromatography on silica (eluant EtOAc:pet. ether 50:50); yield 0.36 g (37%).

15C. 1-(4-[Aminomethyl]-3-methylbenzoyl)-2,3,4,5-tetrahydro-1H-1,5-benzodiazepine hydrochloride The cyanobenzoyl benzodiazepine from Example 15B (0.36 g, 1.24 mmol) was hydrogenated according to the procedure in Example 1B. The product was isolated as the HCl salt; yield 0.17 g (40%).

15D. 1-(4-[3-(2,6-Difluorophenyl)ureidomethyl]-3-methylbenzoyl)-2,3,4,5-tetrahydro-1H-1,5-benzodiazepine The amine hydrochloride from Example 15C (0.170 g, 0.46 mmol) was reacted with 2,6-difluorophenylisocyanate (0.071 g, 0.46 mmol) according to the procedure in Exampl 1C. The product was purified by flash chromatography on silica (eluant EtOAc:pet. ether 80:20); yield 0.089 g (43%).

M.S.: calc m/e=450.19. found [M+H]$^+$=451.2.

Example 16

1-(4-[3-(2,6-Difluorophenyl)ureidomethyl]-3-methylbenzoyl)-5-(3-pyridyl)methyl-2,3,4,5-tetrahydro-1H-1,5-benzodiazepine

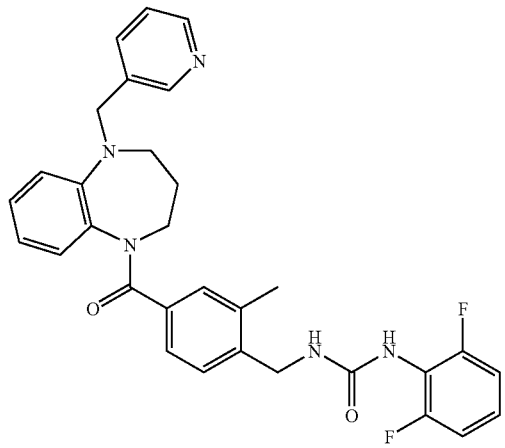

16A. 1-(3-Pyridyl)methyl-2,3,4,5-tetrahydro-1H-1,5-benzodiazepine

To solution of 2,3,4,5-tetrahydro-1H-1,5-benzodiazepine from Example 15A (0.50 g, 3.38 mmol) in 1% acetic acid/methanol (25 ml), at room temperature, was added pyridine-3-carboxaldehyde (0.35 ml, 03.72 mmol). The mixture was stirred at reflux for 18 h and then allowed to cool to room temperature. Sodium borohydride (0.050 g, 0.80 mmol) was added. The mixture was stirred for 2 h and then evaporated in vacuo. The residue was partitioned between EtOAc and saturated sodium bicarbonate solution. The organic layer was washed with brine, dried over MgSO$_4$, and concentrated in vacua. The residue was purified by flash chromatography on silica (eluant EtOAc) to give a white solid; yield 0.386 g (40%).

16B. 1-(4-Cyano-3-methylbenzoyl)-5-(3-pyridyl)methyl-2,3,4,5-tetrahydro-1H-1,5-benzodiazepine The carboxylic acid from Example C (0.31 g, 1.93 mmol) was reacted with 1-(3-pyridyl)methyl-2,3,4,5-tetrahydro-1H-1,5-benzodiazepine from Example 16A (0.39 g, 1.61 mmol) according to the procedure in Example 1A. The product was purified by flash chromatography on silica (eluant EtOAc); yield 0.28 g (45%).

16C. 1-(4-Aminomethyl-3-methylbenzoyl)-5-(3-pyridyl)methyl-2,3,4,5-tetrahydro-1H-1,5-benzodiazepine To a solution of the nitrile from Example 16B (0.28 g, 0.72 mmol) in methanol (20 ml) were added cobaltous chloride (0.338 g, 1.42 mmol) and sodium borohydride (0.27 g, 7.20 mmol). The mixture was stirred at room temperature for 1 h and then saturated aqueous ammonium chloride solution (10 ml) was added. The mixture was concentrated in vacuo and the aqueous residue was partitioned between diethyl ether and water. The aqueous layer was basified by addition of saturated sodium bicarbonate solution and extracted with chloroform (3 times). The combined organic extracts were washed with brine, dried over MgSO$_4$, and concentrated in vacuo to give a white solid; yield 0.20 g (7.2%).

16D. 1-(4-[3-(2,6-Difluorophenyl)ureidomethyl]-3-methylbenzoyl)-5-(3-pyridyl)methyl-2,3,4-tetrahydro-1H-1,5-benzodiazepine The amine from Example 16C (0.065 g, 0.168 mmol) was reacted with 2,6-difluorophenylisocyanate (0.027 g, 0.17 mmol) according to the procedure in Example 1C. The product was purified by flash chromatography on silica (eluant EtOAc); yield 0.068 g (75%).

M.S.: calc m/e=541.23. found [M+H]$^+$=542.2.

Example 17

1-(4-[3-(2,6Difuorophenyl)ureidomethyl]-3-methylbenzoyl)-5-(2-hydroxyethyl)-2,3,4,5-tetrahydro-1H-1,5-benzodiazepine

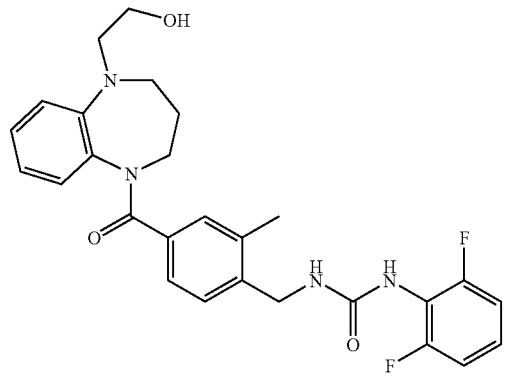

17A. Methyl (2-oxo-2,3,4,5-tetrahydro-1H-1,5-benzodiazepin-1-yl)acetate

To a solution of 1,3,4,5-tetrahydro-benzo[b][1,4]diazepin-2-one (5.0 g, 30.8 mmol) in DMF (30 ml), at −10° C., was added sodium hydride (1.35 g, 60% dispersion, 33.9 mmol). The mixture was stirred at −10° C. for 15 min, then methyl bromoacetate (2.92 ml, 30.8 mmol) was added. The mixture was stirred at −10° C. for a further 1 h and then concentrated in vacuo. The residue was taken up in EtOAc and washed with brine (3 times), dried over MgSO$_4$, and concentrated in vacuo. The residue was purified by flash chromatography on silica (eluant EtOAc) to give a white solid; yield 7.08 g (98%).

17B. 2-(2,3,4,5-Tetrahydro-1H-1,5-benzodiazepin-1-yl)ethanol

Methyl (2-oxo-[1,3,4,5-tetrahydro-benzo[b]1,4]diazepin-1-yl)-acetate from Example 17A (7.08 g, 30.2 mmol) was reduced with lithium aluminium hydride according to the procedure in Example 15A; yield 4.33 g (75%).

17C. 1-(4-Cyano-3-methylbenzoyl)-5-(2-hydroxyethyl)-2,3,4,5-tetrahydro-1H-1,5-benzodiazepine To a solution of the carboxylic acid from Example 1C (1.38 g, 8.58 mmol) in dichloromethane (50 ml) was added thionyl chloride (3.33 ml, 43.0 mmol). The mixture was stirred at reflux for 2 h and then evaporated in vacuo, azeotroping with toluene (2 times). The residue was dissolved in dichloromethane (50 ml) and 2-(2,3,4,5-tetrahydro-1H-1,5-benzodiazepin-1-yl)ethanol from Example 17B (1.5 g, 7.80 mmol) was added. The mixture was stirred at room temperature for 18 h and then evaporated in vacuo. The residue was partitioned between EtOAc and saturated sodium bicarbonate solution. The organic layer was washed with brine, dried over MgSO$_4$, and concentrated in vacuo. The residue was triturated with EtOAc and the resultant solid filtered off; yield 1.25 g (48%).

17D. 1-(4-Aminomethyl-3-methylbenzoyl)-5-(2-hydroxyethyl)-2,3,4,5-tetrahydro-1H-1,5-benzodiazepine The cyanobenzoyl benzodiazepine from Example 17C (1.25 g, 3.73 mmol) was hydrogenated according to the procedure in Example 1B. The product was isolated as the free base; yield 0.94 g (74%).

17E. 1-(4-[3-(2,6-Difluorophenyl)ureidomethyl]-3-methylbenzoyl)-5-(2-hydroxyethyl)-2,3,4,5-tetrahydro-1H-1,5-benzodiazepine The amine from Example 17D (0.94 g, 2.76 mmol) was reacted with 2,6-difluorophenylisocyanate (0.47 g, 3.04 mmol) according to the procedure in Example 1C. The product was purified by flash chromatography on silica (eluant EtOAc); yield 0.068 g (75%).
M.S.: calc m/e=494.21. found [M+H]$^{30}$ =495.2.

Example 18

1-(3-Chloro-4-[3-(2,6-difluorophenyl)ureidomethyl]benzoyl)-5-methyl-2,3,4,5-tetrahydro-1H-1,5-benzodiazepine

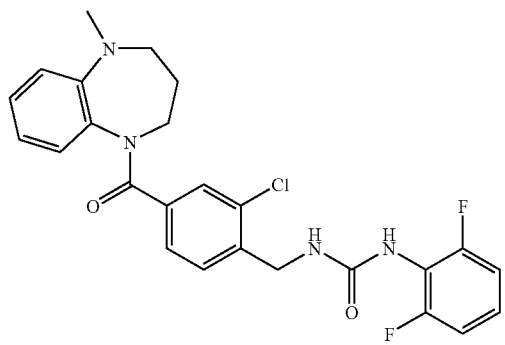

18A. 1-Methyl-2-oxo-2,3,4,5-tetrahydro-1H-1,5-benzodiazepine

To a solution of 2,3,4,5-tetrahydro-1H-1,5-benzodiazepin-2-one (2.0 g, 12.3 mmol) in DMF (30 ml), at −10° C., was added sodium hydride (0.54 g, 60% dispersion, 13.6 mmol). The mixture was stirred at −10° C. for 15 min, then methyl iodide (0.77 ml, 12.3 mmol) was added. The mixture was stirred at −100° C. for a further 1 h and then concentrated in vacuo. The residue was taken up in EtOAc and washed with brine (3 times), dried over MgSO$_4$, and concentrated in vacuo. The residue was purified by flash chromatography on silica (eluant EtOAc) to give a white solid; yield 1.70 g (78%).

18B. 1-Methyl-2,3,4,5-tetrahydro-1H-1,5-benzodiazepine

1-Methyl-2-oxo-2,3,4,5-tetrahydro-1H-1,5-benzodiazepine from Example 18A (1.7 g, 9.65 mmol) was reduced with lithium aluminium hydride according to the procedure in Example 15A; yield 1.34 g (86%).

18C. 1-(4-[tert-Butyloxycarbonylaminomethyl]-3-chlorobenzoyl)-5-methyl-2,3,4,5-tetrahydro-1H-1,5-benzodiazepine The carboxylic acid from Example A2 (0.506 g, 1.77 mmol) was reacted with 1-methyl-2,3,4,5-tetrahydro-1H-1,5-benzodiazepine from Example 18B (0.24 g, 1.48 mmol) according to the procedure in Example 1A. The product was purfied by flash chromatography on silica (eluant EtOAc: pet. ether 50:50); yield 0.30 g (47%).

18D. 1-(4-Aminomethyl-3-chlorobenzoyl)-5-methyl-2,3,4,5-tetrahydro-1H-1,5-benzodiazepine The BOC-aminomethylbenzoyl benzazodiazepine from Example 18C (0.30 g, 0.698 mmol) was reacted according to the procedure in Example 4B. The product was isolated as the HCl salt; yield 0.25 g (98%).

18E. 1-(3-Chloro-[4-3-(2,6-difluorophenyl)ureidomethyl]benzoyl)-5-methyl-2,3,4,5-tetrahydro-1H-1,5-benzodiazepine The amine hydrochloride from Example 18D (0.060 g, 0.164 mmol) was reacted with 2,6-difluorophenylisocyanate (0.021 g, 0.164 mmol) according to the procedure in Example 1C. The product was purified by trituration with diethyl ether to give a white solid; yield 0.058 g (87%).
M.S.: calc m/e=484.15. found [M+H]$^+$; $^{35}$Cl=485.1.

Example 19

1-(4-[3-(2,6-Difluorophenyl)uredomethyl]-2-methyl-benzoyl)-5-methyl-2,3,4,5-tetrahydro-1H-1,5-benzodiazepine

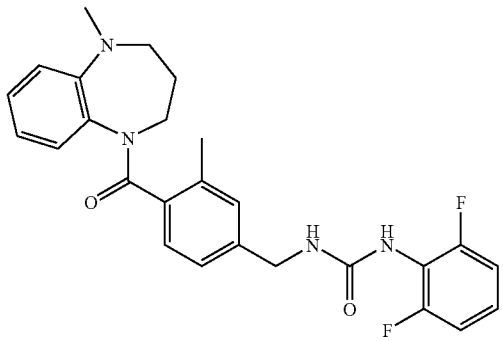

19A. 1-(4-Cyano-2-methylbenzoyl)-5-methyl-2,3,4,5-tetrahydro-1H-1,5-benzodiazepine hydrochloride The carboxylic acid from Example D (0.50 g, 3.10 mmol) was reacted with 1-methyl-2,3,4,5-tetrahydro-1H-1,5-benzodiazepine from Example 18B (0.46 g, 2.80 mmol) according to the procedure in Example 1A. The product was purified by flash chromatography on silica (eluant EtOAc:pet. ether 30:70–70:30); yield 0.27 g (32%).

19B. 1-(4-Aminomethyl-2-methylbenzoyl)-5-methyl-2,3,4,5-tetrahydro-1H-1,5-benzodiazepine hydrochloride The cyanobenzoyl benzazepine from Example 19A (0.26 g, 0.88 mmol) was hydrogenated according to the procedure in Example 1B. The product was isolated as the HCl salt; yield 0.30 g (99%).

19C. 1-(4-[(2,6-Difluorophenyl)ureidomethyl]-2-methylbenzoyl)-5-methyl-2,3,4,5-tetrahydro-1H-1,5-benzodiazepine The amine hydrochloride from Example 19B (0.060 g, 0.17 mmol) was reacted with 2,6-difluorophenylisocyanate (0.027 g, 0.17 mmol) according to the procedure in Example 1C. The product was purified by flash chromatography on silica (eluant EtOAc:pet. ether 80:20); yield 0.070 g (93%).
M.S.: calc m/e=464.20. found [M+H]$^+$=465.2.

Example 20

1-(4-[3-(2,6-Difluorophenyl)uredorethyl]-3,5-dimethylbenzoyl)-2,3,4,5-tetrahydro-1H-1-benzazepine

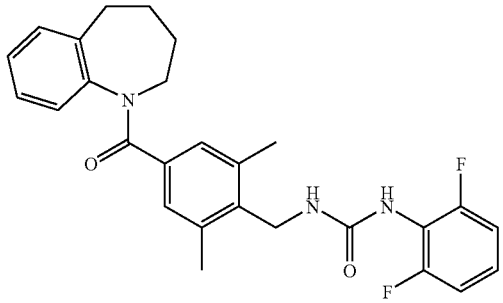

20A. 1-(4-Cyano-3,5-dimethylbenzoyl)-2,3,4,5-tetrahydro-1H-1-benzazepine

The carboxylic acid from Example I2 (0.49 g, 2.80 mmol) was reacted with 2,3,4,5-tetrahydro-1H-1-benzazepine (0.39 g, 2.63 mmol) according to the procedure in Example 17C. The product was purified by flash chromatography on silica (eluant EtOAc:pet. ether 30:70); yield 0.66 g (77%).

20B. 1-(4-Aminomethyl-3,5-dimethylbenzoyl)-2,3,4,5-tetrahydro-1H-1-benzazepine The nitrile from Example 20A (0.65 g, 2.12 mmol) was reduced according to the procedure in Example 16C; yield 0.42 g (64%).

20C. 1-(4-[3-(2,6-Difluorophenyl)ureidomethyl]-3,5-dimethylbenzoyl)-2,3,4,5-tetrahydro-1H-1-benzazepine The amine from Example 20B (0.070 g, 0.23 mmol) was reacted with 2,6-difluorophenylisocyanate (0.043 g, 0.28 mmol) according to the procedure in Example 1C. The product was purified by flash chromatography on silica (eluant EtOAc:pet. ether 40:60); yield 0.033 g (31%).
M.S.: calc m/e=463.21. found [M+H]$^+$=464.2.

Example 21

1-(2-Chloro-6-[3-(2,6-difluorophenyl)ureidomethyl]nicotinoyl)-2,3,4,5-tetrahydro-1H-1-benzazepine

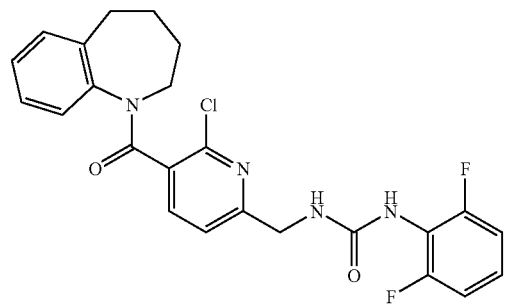

21A. 1-(6-[tert-Butylaminomethyl]-2-chloronicotinoyl)-2,3,4,5-tetrahydro-1H-1-benzazepine The carboxylic acid from Example F3 (0.50 g, 1.74 mmol) was reacted with 2,3,4,5-tetrahydro-1H-1-benzazepine (0.26 g, 1.74 mmol) according to the procedure in Example 1A. The product was purified by flash chromatography on silica (eluant EtOAc:pet. ether 55:45); yield 0.038 g (5%).

21B. 1-(6-Aminomethyl-2-chloronicotinoyl)-2,3,4,5-tetrahydro-1H-1-benzazepine hydrochloride The BOC-aminomethylnicotinoyl benzazepine from Example 21A (0.036 g, 0.074 mmol) was reacted according to the procedure in Example 4B. The product was isolated as the HCl salt; yield 0.026 g (98%).

21C. 1-(2-Chloro-6-[(2,6-difluorophenyl)ureidomethyl]nicotinoyl)-2,3,4,5-tetrahydro-1H-1-benzazepine The amine hydrochloride from Example 21B (0.026 g, 0.073 mmol) was reacted with 2,6-difluorophenylisocyanate (0.014 g, 0.08 mmol) according to the procedure in Example 1C. The product was purified by flash chromatography on silica (eluant EtOAc:pet. ether 90:10); yield 0.031 g (90%).
M.S.: calc m/e=470.13. found [M+H]$^+$; $^{35}$Cl=471.1.

Example 22

1-(6-[3-(2,6-Difluorophenyl)ureidomethyl]-1-methyl-2-oxo-1,2-dihydropyridyl-3-carbonyl)-2,3,4,5-tetrahydro-1H-1-benzazepine

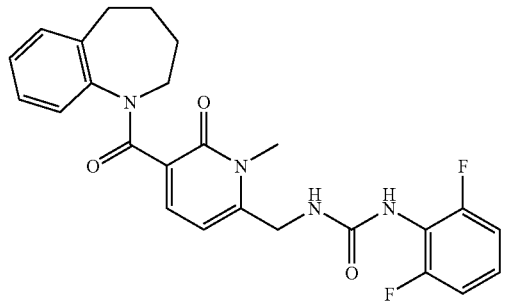

22A. 1-(4/5-Bromo-6-[tert-butyloxycarbonylaminomethyl]-1-methyl-2-oxo-1,2-dihydropyridyl-3-carbonyl)-2,3,4,5-tetrahydro-1H-1-benzazepine The carboxylic acid from Example H3 (1.30 g, 3.60 mmol) was reacted with 2,3,4,5-tetrahydro-1H-1-benzazepine (0.53 g, 3.60 mmol) according to the procedure in Example 1A. The product was purified by flash chromatography on silica (eluant EtOAc:pet. ether 60:40); yield 0.70 g (40%).

22B. 1-(4/5-Bromo-6-[tert-butyloxycarbonylaminomethyl]-1-methyl-2-oxo-1,2-dihydropyridyl-3-carbonyl)-2,3,4,5-tetrahydro-1H-1-benzazepine The benzazepine from Example 22A (0.60 g, 1.23 mmol) was hydrogenated according to the procedure in Example 12A; yield 0.50 g (99%).

22C. 1-(6-Aminomethyl-1-methyl-2-oxo-1,2-dihydropyridyl-3-carbonyl)-2,3,4,5-tetrahydro-1H-1-benzaz pin hydrochloride The BOC-aminomethyl pyridone from Example 22B (0.50 g, 1.22 mmol) was reacted according to the procedure in Example 4B. The product was isolated as the HCl salt; yield 0.43 g (99%).

22D. 1-(6-[3-(2,6-Difluorophenyl)ureidomethyl]-1-methyl-2-oxo-1,2-dihydropyridyl-3-carbonyl)-2,3,4,5-tetrahydro-1H-1-benzazepine The amine hydrochloride from Example 22C (0.050 g, 0.144 mmol) was reacted with 2,6-difluorophenylisocyanate (0.025 g, 0.144 mmol) according to the procedure in Example 1C. The product was purified by flash chromatography on silica (eluant EtOAc:methanol 90:10); yield 0.064 g (95%).
M.S.: calc m/e=466.18. found [M+H]$^+$=467.2.

Example 23

1-(4-[3-(2,6-Difluorophenyl)ureidomethyl]-3-methylbenzoyl)-5-ethyl-2,3,4,5-tetrahydro-1H-1,5-benzodiazepine

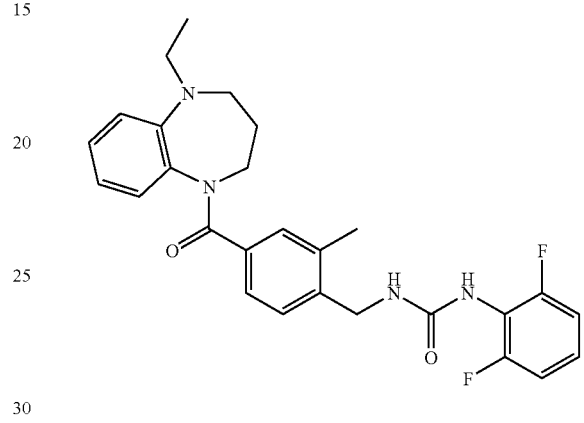

23A. 1-Ethyl-2-oxo-2,3,4,5-tetrahydro-1H-1,5-benzodiazepine

2-Oxo-2,3,4,5-tetrahydro-1H-1,5-benzodiazepine (1.95 g, 11.96 mmol) was reacted with ethyl iodide (1.4 ml, 17.5 mmol) according to the procedure in Example 18A. The product was purified by flash chromatography on silica (eluant EtOAc); yield 1.70 g (75%).

23B. 1-Ethyl-2,3,4,5-tetrahydro-1H-1,5-benzodiazepine

1-Ethyl-2-oxo-2,3,4,5-tetrahydro-1H-1,5-benzodiazepine from Example 23A (1.7 g, 8.94 mmol) was reduced with lithium aluminium hydride according to the procedure in Example 15A; yield 1.55 g (98%).

23C. 1-(4-Cyano-3-methylbenzoyl)-5-ethyl-2,3,4,5-tetrahydro-1H-1,5-benzodiazepine The carboxylic acid from Example C (0.53 g, 3.29 mmol) was reacted with 1-ethyl-2,3,4,5-tetrahydro-1H-1,5-benzodiazepine from Example 23B (0.514 g, 2.92 mmol) according to the procedure in Example 1A. The product was purified by flash chromatography on silica (eluant EtOAc: pet. ether 60:40); yield 0.55 g (59%).

23D. 1-(4-Aminomethyl-3-methylbenzoyl)-5-ethyl-2,3,4,5-tetrahydro-1H-1,5-benzodiazepine hydrochloride The nitrile from Example 23C (0.55 g, 1.73 mmol) was hydrogenated according to the procedure in Example 1B. The product was isolated as the HCl salt; yield 0.60 g (96%).

23E. 1-(4-[3-(2,6-Difluorophenyl)ureidomethyl]-3-methylbenzoyl)-5-ethyl-2,3,4,5-tetrahydro-1H-1,5-benzodiazepine The amine hydrochloride from Example 23D (0.071 g, 0.20 mmol) was reacted with 2,6-difluorophenylisocyanate (0.038 g, 0.25 mmol) according to the procedure in Example 1C. The product was purified by flash chromatography on silica (eluant EtOAc:pet. ether 50:50–100:0); yield 0.044 g (46%).

M.S.: calc m/e=478.22. found [M+H]$^+$=479.2.

Example 24

5-(4-[3-(2,6-Difluorophenyl)ureidomethyl]-3-methylbenzoyl-6,7,8,9-tetrahydro-5H-pyrido[2,3-b]azepine

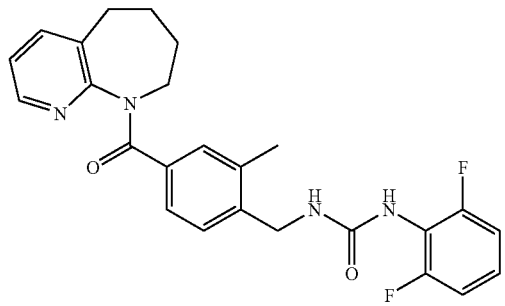

24A. 5-(4-Cyano-3-methylbenzoyl)-6,7,8,9-tetrahydro-5H-pyrido[2,3b]azepine

The carboxylic acid from Example C (0.36 g, 2.26 mmol) was reacted with 6,7,8,9-tetrahydro-5H-pyrido[2,3-b]azepine (0.33 g, 2.23 mmol) according to the procedure in Example 17C. The product was purified by flash chromatography on silica (eluant EtOAc:pet. ether 80:20); yield 0.47 g (73%).

24B. 5-(4-Aminomethyl-3-methylbenzoyl)-6,7,8,9-tetrahydro-5H-pyrido[2,3-b]azepine The cyanobenzoyl pyridoazepine from Example 24A (0.46 g, 1.58 mmol) was hydrogenated according to the procedure in Example 1B. The product was isolated as the free base; yield 0.28 g (60%).

24C. 5-(4-[3-(2,6-Difluorophenyl)ureidomethyl]-3-methylbenzoyl)-6,7,8,9-tetrahydro-5H-pyrido[2,3-b]azepine The amine from Example 24B (0.071 g, 0.20 mmol) was reacted with 2,6-difluorophenylisocyanate (0.035 g, 0.23 mmol) according to the procedure in Example 1C. The product was purified by flash chromatography on silica (eluant EtOAc); yield 0.020 g (19%).

M.S.: calc m/e=450.19. found [M+H]$^+$=451.2.

Example 25

5-(4-[3-(2,6-Difluorophenyl)ureidomethyl]-3-methylbenzoyl)-1-oxo-1$\lambda^4$-2,3,4,5-tetrahydro-1,5-benzothiazepine

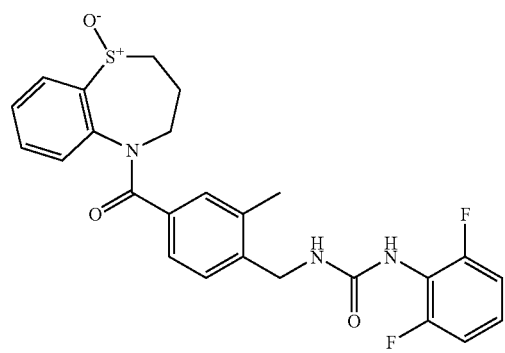

25A. 5-(4-Cyano-3-methylbenzoyl)-2,3,4,5-tetrahydro-1,5-benzothiazepine

The carboxylic acid from Example C (0.27 g; 1.68 mmol) was reacted with 2,3,4,5-tetrahydro-1,5-benzothiazepine (0.28 g, 1.70 mmol) according to the procedure in Example 1A. The product was purified by flash chromatography on silica (eluant EtOAc:pet. ether 60:40); yield 0.43 g (84%).

25B. 5-(4-Aminomethyl-3-methylbenzoyl)-2,3,4,5-tetrahydro-1,5-benzothiazepine The cyanobenzoyl benzothiazepine from Example 25A (0.43 g, 1.40 mmol) was hydrogenated according to the procedure in Example 1B. The product was isolated as the free base; yield 0.10 g (29%).

25C. 5-(4-[3-(2,6-Difluorophenyl)ureidomethyl]-3-methylbenzoyl)-2,3,4,5-tetrahydro-1,5-benzothiazepine The amine from Example 25B (0.10 g, 0.32 mmol) was reacted with 2,6-difluorophenylisocyanate (0.061 g, 0.39 mmol) according to the procedure in Example 1C. The product was purified by trituration with diethyl ether to give a white solid; yield 0.112 g (75%).

25D. 5-(4-[3-(2,6-Difluorophenyl)ureidomethyl]-3-methylbenzoyl)-1-oxo-1$\lambda^4$-2,3,4,5-tetrahydro-1,5-benzothiazepine To a suspension of the thiazepine from Example 25C (0.15 g, 0.33 mmol) in methanol (40 ml), dichloromethane (10 ml) and water (10 ml) was added sodium periodate (0.21 g, 0.99 mmol). The mixture was stirred at room temperature for 70 h and then filtered. The filtrate was evaporated in vacuo and the residue was purified by flash chromatography on silica (eluant EtOAc); yield 0.013 g (8%).

M.S.: calc m/e=483.14. found [M+H]$^+$=484.1.

Example 26

4-(4-[3-(2,6-Difluorophenyl)ureidomethyl]-3-methylbenzoyl)-5,6,7,8-tetrahydro-4H-thieno[3,2-b]azepine

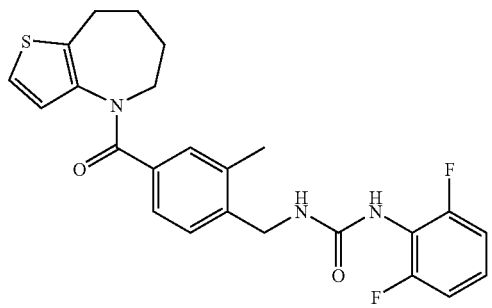

26A. 4-(4-Cyano-3-methylbenzoyl)-5,6,7,8-tetrahydro-4H-thieno[3,2-b]azepine The carboxylic acid from Example C (0.50 g, 3.10 mmol) was reacted with 5,6,7,8-tetrahydro-4H-thieno[3,2-b]azepine (0.45 g, 2.95 mmol) according to the procedure in Example 1A. The product was purified by recrystallisation from EtOAc:pet. ether; yield 0.48 g (55%).

26B. 4-(4-Aminomethyl-3-methylbenzoyl)-5,6,7,8-tetrahydro-4H-thieno[3,2-b]azepine The nitrile from Example 26A (0.48 g, 1.60 mmol) was reduced according to the procedure in Example 16C; yield 0.169 (33%).

26C. 4-(4-[3-(2,6-Difluorophenyl)ureidomethyl]-3-methylbenzoyl)-5,6,7,8-tetrahydro-4H-thieno[3,2-b]azepine The amine from Example 26B (0.05 g, 0.18 mmol) was reacted with 2,6difluorophenylisocyanate (0.027 g, 0.18 mmol) according to the procedure in Example 1C. The product was purified by tituration with diethyl ether to give a white solid; yield 0.052 g (67%).

M.S.: calc m/e=455.15 found [M+H]$^+$=456.1.

Example 27

4-(3-Methyl-4-[3-(2,3,5,6-tetrafluorophenyl)ureidomethyl]benzoyl)-5,6,7,8-tetrahydro-4H-thieno[3,2-b]azepine

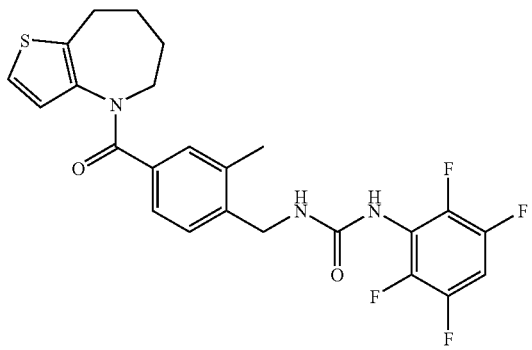

The amine from Example 26B (0.062 g, 0.206 mmol) was reacted with 2,3,5,6-tetrafluorophenylisocyanate (0.079 g, 0.413 mmol, prepared from the aniline according to the procedure of Kurita. K, et al., *J. Org. Chem.*, 41, 1976, p2070.) according to the procedure in Example 1C. The product was purified by flash chromatography on silica (eluant EtOAc:pet. ether 50:50); yield 0.045 g (44%).

M.S.: calc m/e=491.13 found [M+H]$^+$=492.1.

Example 28

1-(4-[N-(4-Methoxy-4-oxobutanoyl)aminomethyl]-3-methylbenzoyl-2,3,4,5-tetrahydro-1H-1-benzazepine

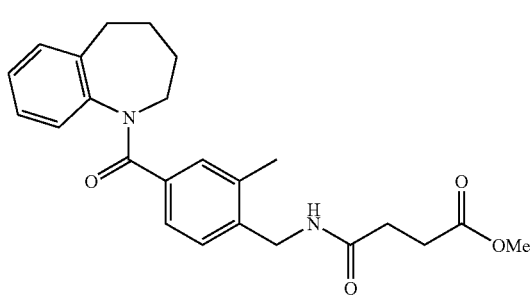

28A. 1-(4-Cyano-3-methylbenzoyl)-2,3,4,5-tetrahydro-1H-1-benzazepine

To a solution of 2,3,4,5-tetrahydro-1H-1-benzazepine (0.80 g, 5.44 mmol) in dichloromethane (40 ml) were added 4-cyano-3-methylbenzoic acid from example C (0.96 g, 5.95 mmol), triethylamine (0.76 g, 5.44 mmol), 4-(dimethylamino)pyridine (0.66 g, 5.44 mmol) and WSCDI (2.17 g, 10.88 mmol). The mixture was stirred at reflux for 18 h, cooled and evaporated in vacuo. The residue was partitioned between EtOAc and 1M KHSO$_4$. The organic layer was washed with saturated sodium bicarbonate solution and brine, dried over MgSO$_4$, and concentrated in vacuo. The residue was purified by flash chromatography on silica (eluant EtOAc:pet. ether 30:70); yield 1.10 g (70%).

28B. 1-(4-[Aminomethyl]-3-methylbenzoyl)-2,3,4,5-tetrahydro-1H-1-benzazepine hydrochloride To a degassed solution of the cyanobenzoyl benzazepine from Example 28A (1.10 g, 3.79 mmol) in methanol (40 ml) were added concentrated hydrochloric acid (0.98 ml, 11.3 mmol) and 10% palladium-on-carbon (0.80 g). Hydrogen gas was bubbled through the mixture for 5 h at room temperature. The catalyst was removed by filtration through a pad of celit and the filtrate was evaporated in vacuo to give the product as the HCl salt; yield 1.23 g (98%).

28C. 1-(4-[N-(4-Methoxy-4-oxobutanoyl)aminomethyl]-3-methylbenzoyl)-2,3,4,5-tetrahydro-1H-1-benzazepine To a solution of the amine from Example 28B (0.10 g, 0.30 mmol) in dichioromethane (10 ml) were added triethylamine (0.061 ml, 0.90 mmol) and 3-carbomethoxy propionyl chloride (0.046 g, 0.30 mmol). The mixture was stirred at room temperature for 18 h and then washed with 1M KHSO$_4$ (3 times), water and brine, dried over Na$_2$SO$_4$, and concentrated in vacuo to give a white solid; yield 0.10 g (81%).

M.S.: calc m/e=408. found [M+H]$^+$=409.

Example 29

1-(4-[N-(2-Methoxy-2-oxoethanoyl)aminomethyl]-3-methylbenzoyl)-2,3,4,5-tetrahydro-1H-1-benzazepine

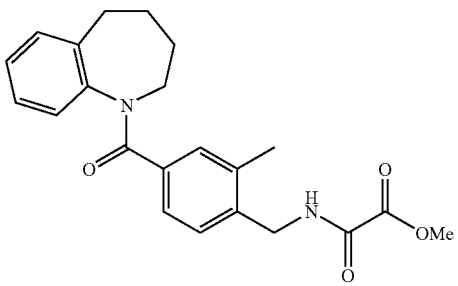

The amine hydrochloride from Example 28B (0.10 g, 0.30 mmol) was reacted with methyl oxalyl chloride (0.037 g, 0.30 mmol) according to the procedure in Example 28C to give a white solid; yield 0.085 g (76%).

M.S.: calc m/e=380. found [M+H]$^+$=381.

Example 30

1-(4-[N-(2-Hydroxy-2-oxoethanoyl)aminomethyl]-3-methylbenzoyl)-2,3,4,5-tetrahydro-1H-1benzazepine

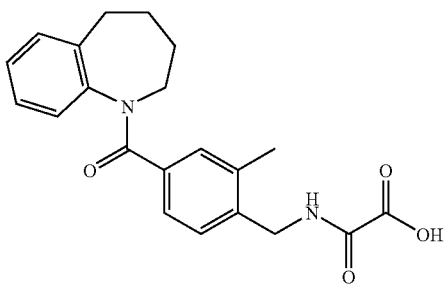

To a solution of the methyl ester from Example 29 (0.045 g, 0.118 mmol) in THF (10 ml) and water (5 ml) was added lithium hydroxide monohydrate (0.010 g, 0.23 mmol). The mixture was stirred at room temperature for 2 h, acidified to pH1 by addition of 1M HCl and extracted with EtOAc (3 times). The combined organic extracts were washed with brine, dried over Na$_2$SO$_4$, and concentrated in vacuo to give a white solid; yield 0.034 g (76%).

M.S.: calc m/e=366. found [M+H]$^+$=367.

Example 31

1-(4-[N-(5-Methoxy-5-oxopentanoyl)aminomethyl]-3-methylbenzoyl)-2,3,4,5-tetrahydro-1H-1-benzazepine

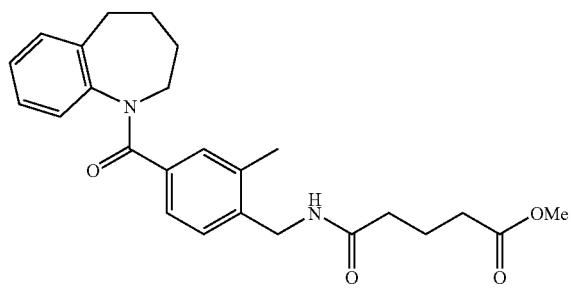

The amine hydrochloride from Example 28B (0.10 g, 0.30 mmol) was reacted with methyl 4-(chloroformyl) butyrate (0.050 g, 0.30 mmol) according to the procedure in Example 1C to give a white solid; yield 0.061 g (48%).

M.S.: calc m/e=422. found [M+H]$^+$=423.

Example 32

1-(4-[N-(2-Ethoxy-2-oxoethylcarbamoyl)aminomethyl]-3-methylbenzoyl)-2,3,4,5-tetrahydro-1H-1-benzazepine

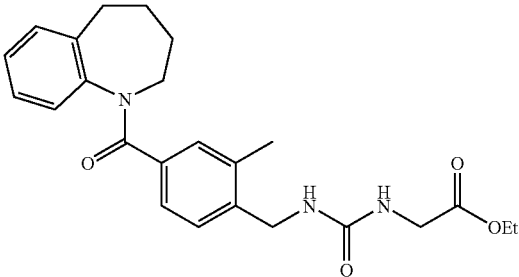

To a solution of the amine from Example 28B (0.10 g, 0.30 mmol) in dichloromethane (10 ml) were added triethylamine (0.061 ml, 0.90 mmol) and ethyl isocyanatoacetate (0.059 g, 0.45 mmol). The mixture was stirred at room temperature for 18 h and then washed with 1M KHSO$_4$ (3 times), water and brine, dried over Na$_2$SO$_4$, and concentrated in vacuo to give a white solid; yield 0.10 g (81%).

M.S.: calc m/e=423. found [M+H]$^+$=424.

Example 33

1-(4-[N-(Carboxymethylcarbamoyl)aminomethyl]-3-methylbenzoyl)-2,3,4,5-tetrahydro-1H-1-benzazepine

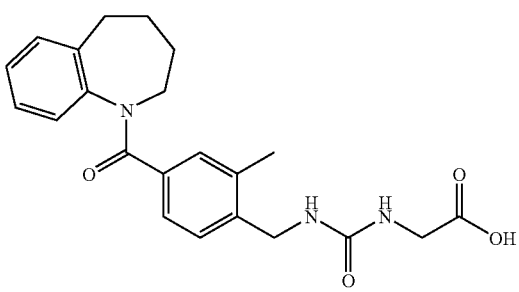

To a solution of the ethyl ester from Example 32 (0.050 g, 0.10 mmol) in THF (20 ml) and water (5 ml) was added lithium hydroxide monohydrate (0.020 g, 0.45 mmol). The mixture was stirred at room temperature for 4 h. The mixture was concentrated in vaicuo and the residue diluted with water then washed with diethyl ether. The aqueous layer was acidified to pH 1 by addition of 1M HCl and extracted with EtOAc (3 times). The combined organic extracts were washed with brine, dried over Na$_2$SO$_4$, and concentrated in vacuo to give a white solid; yield 0.046 g (99%).

M.S.: calc m/e=395. found [M+H]$^+$=396.

Example 34

1-(4-[N-(2-Methylamino-2-oxoethylcarbamoyl)aminomethyl]-3-methylbenzoyl)-2,3,4,5-tetrahydro-1H-1-benzazepine

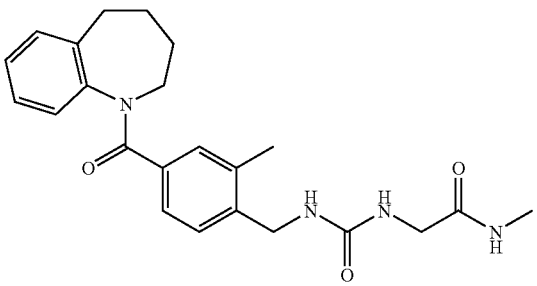

To a solution of the carboxylic acid from Example 33 (0.10 g, 0.25 mmol) in dichloromethane (25 ml) was added DIEA (0.221 ml, 1.26 mmol) and PyBroP (0.129 g, 0.278 mmol). The mixture was stirred at room temperature for 10 min and then methylamine hydrochloride (0.085 g, 1.26 mmol) was added. Stirring was continued for a further 3 h. The mixture was then washed with 1M $KHSO_4$ (3 times), saturated sodium bicarbonate solution (3 times) and brine, dried over $Na_2SO_4$, and concentrated in vacuo. The residue was purified by flash chromatography on silica (eluant dichloromethane:methanol 96:4) to give a white solid; yield 0.018 g (17%).

M.S.: calc m/e=408. found $[M+H]^+$=409.

Example 35

1-(4-[N-(2-Dimethylamino-2-oxoethylcarbamoyl)aminomethyl]-3-methylbenzoyl)-2,3,4,5-tetrahydro-1H-1-benzazepine

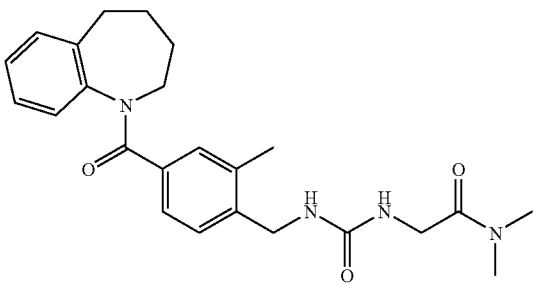

The carboxylic acid from Example 33 (0.07 g, 0.18 mmol) was reacted with dimethylamine hydrochloride (0.072 g, 0.88 mmol) according to the procedure in Example 7. The product was purified by flash chromatography on silica (eluant chloroform:methanol:acetic acid 98:1:1) to give a white solid; yield 0.08 g (11%).

M.S.: calc m/e=422. found $[M+H]^+$=423.

Example 36

1-(4-[N-(2-Methoxy-2-oxoethylcarbamoyl)aminomethyl]-3-methylbenzoyl)-2,3,4,5-tetrahydro-1H-1-benzazepine

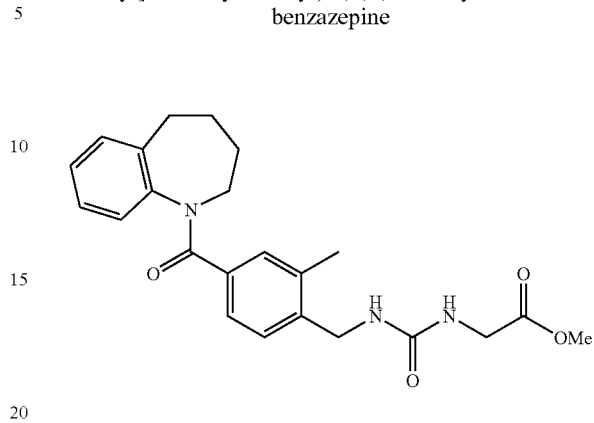

To a solution of the carboxylic acid from Example 33 (0.080 g, 0.20 mmol) under a nitrogen atmosphere in dichloromethane (25 ml) at 0° C. were added DMF (20 □l) and oxalyl chloride (31 mg, 0.24 mmol). The mixture was stirred at 0° C. to room temperature for 2 h and then concentrated in vacuo. The residue was dissolved in methanol (4 ml) and dichloromethane (16 ml) and the mixture stirred at room temperature for 16 h. The mixture was then washed with 1M $KHSO_4$ (3 times), saturated sodium bicarbonate solution (3 times) and brine, dried over $Na_2SO_4$, and concentrated in vacuo. The residue was purified by flash chromatography on silica (eluant dichloromethane:methanol 96:4) to give a white solid; yield 0.049 g (60%).

M.S.: calc m/e=409. found $[M+H]^+$=410.

Example 37

1-(4-[N-(2-Amino-2-oxoethylcarbamoyl)aminmethyl]-3-methylbenzoyl)-2,3,4,5-tetrahydro-1H-1-benzazepine

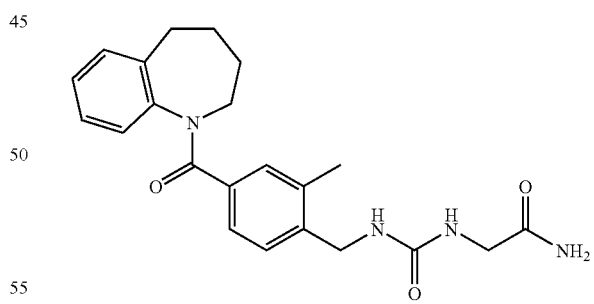

To a solution of the carboxylic acid from Example 33 (0.10 g, 0.25 mmol) in dichloromethane (20 ml) were added hydroxybenzotrazole (34 mg, 0.25 mmol) and WSCDI (51 mg, 0.25 mmol). The mixture was stirred at room temperature for 10 min. Ammonia 880 (0.5 ml) was then added and stirring continued for a further 16 h. The mixture was concentrated in vacuo and the residue purified by flash chromatography on silica (eluant ethyl acetate) to give a white solid; yield 0.008 g (8%).

M.S.: calc m/e=394. found $[M+H]^+$=395.

Example 38

4-(4-[N-(4-Methoxy-4-oxobutanoyl)aminomethyl]-3-chlorobenzoyl)-5,6,7,8-tetrahydro-4H-thieno[3,2-b]azepine

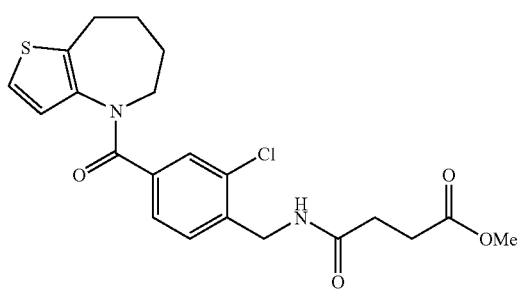

38A. 4-(4-[N-(tert-Butyloxycarbonyl)aminomethyl]-3-chlorobenzoyl)-5,6,7,8-tetrahydro-4H-thieno[3,2-b]azepine hydrochloride The carboxylic acid from Example A2 (0.60 g, 2.10 mmol) was reacted with 5,6,7,8-tetrahydro-4H-thieno[3,2-b]azepine (0.28 g, 1.80 mmol) according to the procedure in example 28A. The product was purified by flash chromatography on silica (eluant EtOAc:pet. ether 40:60) to give a yellow solid.

38B. 4-(4-[Aminomethyl]-3-chlorobenzoyl)-5,6,7,8-tetrahydro-4H-thieno[3,2-b]azepine hydrochloride The BOC amine from Example 38A was dissolved in 4N HCl/dioxan (30 ml). The mixture was stirred at room temperature for 40 min then concentrated in vacuo to leave a tan solid; yield 0.41 g (63%, for 2 steps).

38C. 4-(4-[N-(4-Methoxy-4-oxobutanoyl)aminomethyl]-3-chlorobenzoyl)-5,6,7,8-tetrahydro-4H-thieno[3,2-b]azepine To a solution of the amine from Example 38B (0.032 g, 0.08 mmol) in dichloromethane (10 ml) were added triethylamine (0.025 ml, 0.18 mmol) and 3-carbomethoxypropionyl chloride (0.014 g, 0.08 mmol). The mixture was stirred at room temperature for 18 h and then washed with 1M KHSO$_4$ (3 times), water and brine, dried over Na$_2$SO$_4$, and concentrated in vacuo. The residue was purified by flash chromatography on silica (eluant EtOAc:pet. ether 50:50–90:10); yield 0.022 g (56%).

M.S.: calc m/e=434. found [M+H]$^{+35}$Cl=435.

Example 39

1-(2-Methyl-4-(2,3,4,5-tetrahydro-1-benzazepin-1-ylcarbonyl)benzylcarbamoyl)-L-proline-N,N-dimethylamide

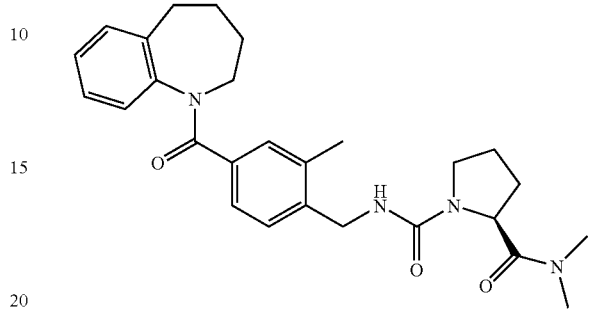

39A. 2-Methyl-4-((2,3,4,5-tetrahydro-1H-benzo[b]azepine)-1-carbonyl)-benzonitrile.

To a solution of 2,3,4,5-tetrahydro-1H-benzo[b]azepine (0.80 g, 5.44 mmol) in dichloromethane (50 ml) were added 4-cyano-3-methylbenzoic acid (0.96 g, 5.95 mmol), triethylamine (0.60 g, 5.95 mmol), 4-(dimethylamino)pyridine (0.73 g, 5.95 mmol) and WSCDI (1.24 g, 6.48 mmol). The mixture was stirred at reflux for 18 h, cooled and evaporated in vacuo. The residue was partitioned between EtOAc and 1M KHSO$_4$. The organic layer was washed with saturated sodium bicarbonate solution and brine, dried over MgSO$_4$, and concentrated in vacuo. The crude material was purified by flash chromatography on silica (eluant EtOAc:pet. ether 30:70); yield 1.10 g (70%).

39B. 1-(4-(Aminomethyl)-3-methylbenzoyl)-2,3,4,5-tetrahydro-1H-benzo[b]azepine hydrochloride.

To a degassed solution of the cyanobenzazepine of Example 39A (1.10 g, 3.79 mmol) in methanol (50 ml) were added concentrated hydrochloric acid (0.98 ml, 11.3 mmol) and 10% palladium on carbon (0.80 g). Hydrogen gas was bubbled through the mixture for 5 h at room temperature. The catalyst was removed by filtering through a pad of celite and the filtrate was evaporated; yield 1.23 g (98%).

39C. 1-(2-Methyl-4-(2,3,4,5-tetrahydro-1-benzazepin-1-ylcarbonyl)benzylcarbamoyl)-L-proline-N,N-dimethylamide To a solution of the amine of Example 39B (0.10 g, 0.302 mmol) in DMF (10 ml), under a nitrogen atmosphere, were added N,N-diisopropylethylamine (43 mg, 0.332 mmol) and carbonyl diimidazole (0.074 g, 0.453 mmol). The mixture was stirred at room temperature for 40 minutes. A solution of proline-N,N-dimethylamide (0.107 g, 0.756 mmol) in DMF (1 ml) was added. The mixture was stirred at room temperature for a further 16 hr. The solvent was removed in vacuo and the crude material was purified by flash chromatography on silica (eluant methanol:dichloromethane 5:95); yield 0.115 g (82%).

M.S.: calc m/e=462.26. found [M+H]$^+$=463.2

Example 40

(4R)-4-Hydroxy-1-(2-methyl-4-(2,3,4,5-tetrahydro-1-benzazepin-1-ylcarbonyl)benzyl-carbamoyl)-L-proline-N,N-dimethylamide

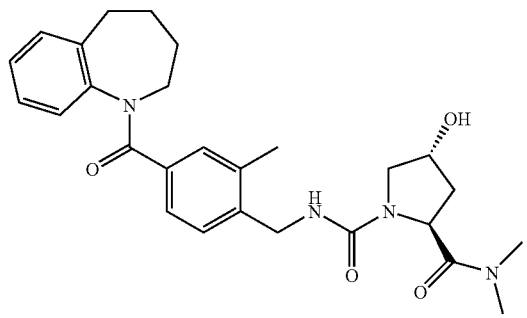

40A. L-trans-4-Hydroxyproline-N,N-dimethylamide hydrochloride

To a solution of BOC-hydroxyproline (2.99 g, 13.89 mmol) in dichloromethane (100 ml) were added N,N-diisopropylethylamine (3.7 ml, 21.24 mmol), 4-(dimethylamino)pyridine (1.74 g, 14.24 mmol), dimethylamine hydrochloride (1.72 g, 21.09 mmol) and WSCDI (3.17 g, 16.68 mmol). The mixture was stirred at room temperature for 30 h. The mixture was diluted with dichloromethane (100 ml) and washed with 0.3M KHSO$_4$, saturated sodium bicarbonate solution and brine, dried over MgSO$_4$, and concentrated in vacuo to give a colourless gum. This crude material was taken up in 4N HCl/dioxan (50 ml) and stirred at room temperature for 1 hr and then concentrat d in vacuo. The residue was azeotroped with toluene and diethyl ether to give a white solid; yield 0.45 g (17%).

40B. (4R)-4-Hydroxy-1-(2-methyl-4-(2,3,4,5-tetrahydro-1-benzazepin-1-ylcarbonyl)benzyl-carbamoyl-L-proline-N,N-dimethylamide.

The amine of Example 39B (0.10 g, 0.302 mmol) was reacted with the amine of Example 40A (0.153 mg, 0.785 mmol) following the method of Example 39C. The product was purified by flash chromatography on silica (eluant chloroform:methanol:acetic acid 95:4:1); yield 0.95 g (66%).

M.S.: calc m/e=478.26. found [M+H]$^+$=479.2

Following the above methods, the following compounds were also prepared.

TABLE A

Examples 41–44

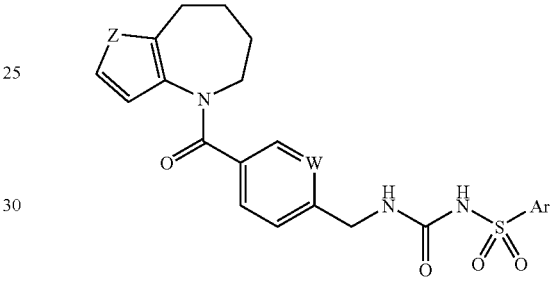

| Ex. | Ar | W | Z | M + H$^+$ |
|-----|--------|----|-------|-------|
| 41 | Ph | N | CH=CH | 465.4 |
| 42 | Ph | CH | S | 470.2 |
| 43 | 4-Me—Ph | CH | CH=CH | 478.1 |
| 44 | 2-Me—Ph | CH | CH=CH | 478.1 |

TABLE B

Examples 45–55

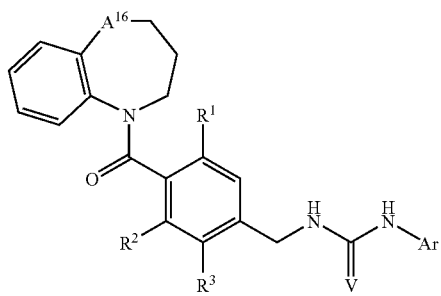

| Ex. | Ar | R$^1$ | R$^2$ | R$^3$ | A$^{16}$ | V | M + H$^+$ |
|-----|---------|---|---|----|---------|---|-------|
| 45 | 2,6-F$_2$—Ph | H | H | H | NCH$_2$Ph | O | 527.4 |
| 46 | 2,6-F$_2$—Ph | H | H | H | S | O | 454 |
| 47 | 1-Nap | H | H | Cl | CH$_2$ | O | 484 |
| 48 | Ph | H | H | Cl | CH$_2$ | O | 434 |

TABLE B-continued

Examples 45–55

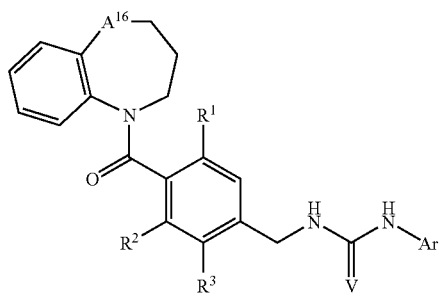

| Ex. | Ar | R¹ | R² | R³ | A¹⁶ | V | M + H⁺ |
|---|---|---|---|---|---|---|---|
| 49 | 3-Pyr | H | H | Me | CH₂ | S | 431.1 |
| 50 | 2,6-F₂—Ph | MeO | H | H | CH₂ | O | 466 |
| 51 | 2,6-F₂—Ph | H | CH:CH—CH:CH | | CH₂ | O | 486 |
| 52 | 2,6-F₂—Ph | H | H | Me | N(CH₂)₂NMe₂ | O | 522.3 |
| 53 | 2,6-F₂—Ph | Cl | H | Cl | CH₂ | O | 504.1 |
| 54 | 2,6-F₂—Ph | H | H | Me | SO₂ | O | 500.2 |
| 55 | 2,6-F₂—Ph | H | H | HMe | NCH₂CO₂H | O | 509.2 |

TABLE C

Examples 56–57

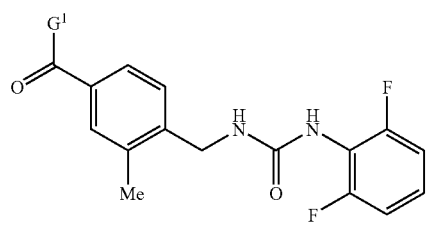

| Ex. | G¹ | M + H⁺ |
|---|---|---|
| 56 | (benzo-fused pyrazolodiazepine) | 488.3 |
| 57 | (N-methylpyrazolo-benzodiazepine) | 517.1 |

TABLE D

Examples 58–61

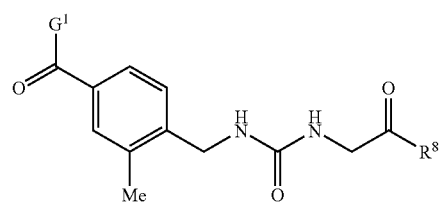

| Ex. | G¹ | R⁸ | M + H⁺ |
|---|---|---|---|
| 58 | (N-methyl-benzodiazepine) | OEt | 439 |
| 59 | (pyrido-benzodiazepine) | NMe₂ | 473.3 |
| 60 | (pyrazolo-benzodiazepine) | NMe₂ | 461.1 |

TABLE D-continued

Examples 58–61

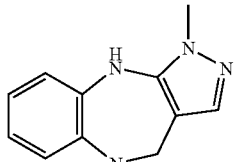

| Ex. | G¹ | R⁸ | M + H⁺ |
|---|---|---|---|
| 61 | (1-methyl-pyrazolo-benzodiazepine) | NMe₂ | 476 |

TABLE E

Examples 62–70

| Ex. | f | R² | R³ | R⁸ | M + H⁺ |
|---|---|---|---|---|---|
| 62 | 1 | H | Me | piperidine | 463 |
| 63 | 1 | H | Me | pyrrolidine | 449.2 |
| 64 | 0 | H | Me | OEt | 410 |
| 65 | 1 | Me | H | OEt | 424 |
| 66 | 1 | H | Me | OiPr | 438 |
| 67 | 1 | H | Me | OtBu | 452 |
| 68 | 1 | H | Cl | NMe₂ | 443 |
| 69 | 2 | H | Me | OEt | 438 |
| 70 | 2 | H | Me | OH | 410 |

TABLE F

Examples 71–77

| Ex. | A¹⁶ | f | R² | R³ | R⁸ | M + H⁺ |
|---|---|---|---|---|---|---|
| 71 | O | 2 | H | H | OMe | 397 |
| 72 | CH₂ | 1 | H | Me | OMe | 415 |
| 73 | CH₂ | 1 | H | Me | OEt | 409 |
| 74 | CH₂ | 1 | H | Me | OH | 381 |
| 75 | CH₂ | 2 | H | Me | OH | 395 |
| 76 | CH₂ | 3 | H | Me | OH | 409 |
| 77 | CH₂ | 1 | Me | H | OMe | 395 |

TABLE G

Examples 78–90

| Ex. | G¹ | R³ | M + H⁺ |
|---|---|---|---|
| 78 | (triazolo-benzodiazepine) | Me | 502 |
| 79 | (tetrahydro-benzazepine) | OMe | 479.2 |
| 80 | (tetrahydro-benzazepine) | Et | 477.3 |
| 81 | (hydroxy-tetrahydro-benzazepine) | Me | 479.2 |

TABLE G-continued

Examples 78–90

| Ex. | G¹ | R³ | M + H⁺ |
|---|---|---|---|
| 82 | (4H-thieno-benzodiazepine) | Me | 518.0 |
| 83 | (N-Me thieno-benzodiazepine, NH) | Me | 532.2 |
| 84 | (thieno-benzazepine) | Me | 517.2 |
| 85 | (pyrido-benzodiazepine, NH) | Me | 513.7 |
| 86 | (N-Me pyrido-benzodiazepine) | Me | 527.0 |
| 87 | (pyrido-benzoxazepine) | Me | 514.6 |
| 88 | (N-Me pyrazolo-benzodiazepine) | Me | 516.1 |
| 89 | (N-Me pyrrolo-benzodiazepine) | Me | 515.0 |
| 90 | (pyrrolo-benzodiazepine fused) | Me | 500.7 |

TABLE H

Examples 91–106

| Ex. | G¹ | E¹ | E² | M + H⁺ |
|---|---|---|---|---|
| 91 | (benzazepine) | H | OAc | 521.0 |
| 92 | (benzazepine) | | =O | 477.3 |
| 93 | (N-Me thieno-benzodiazepine) | H | OBn | 638.2 |
| 94 | (benzazepine) | Br | H | 541.1 |
| 95 | (benzazepine) | F | F | 499.2 |

TABLE H-continued
Examples 91–106
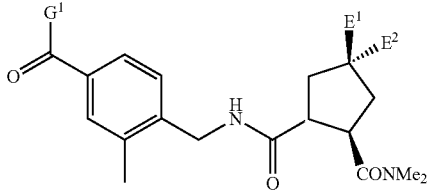
| Ex. | G¹ | E¹ | E² | M + H⁺ |
|---|---|---|---|---|
| 96 | 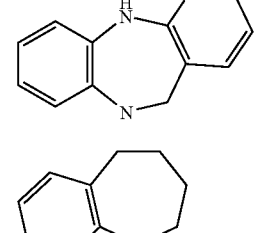 | H | OBn | 619.2 |
| 97 | 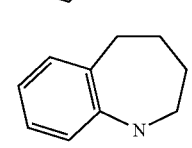 | H | N₃ | 504.3 |
| 98 | 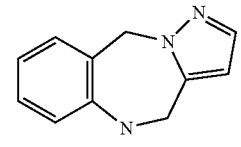 | H | O-tBu | 535.3 |
| 99 | 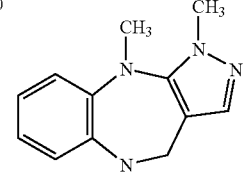 | H | OH | 517.6 |
| 100 | 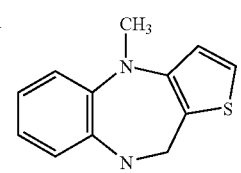 | H | OH | 546.3 |
| 101 | 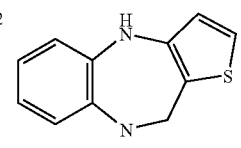 | H | OH | 547.9 |
| 102 | 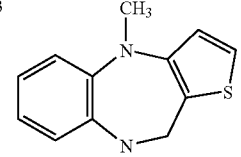 | H | OMe | 548.2 |
| 103 | 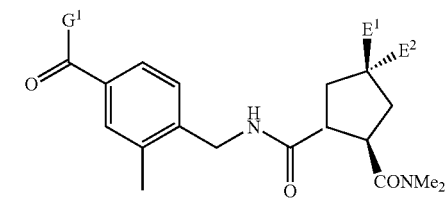 | H | OMe | 562.1 |
TABLE H-continued
Examples 91–106
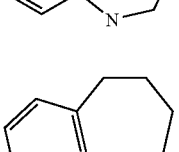
| Ex. | G¹ | E¹ | E² | M + H⁺ |
|---|---|---|---|---|
| 104 | 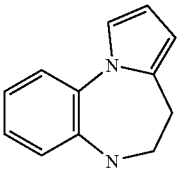 | H | Cl | 566.2 |
| 105 | 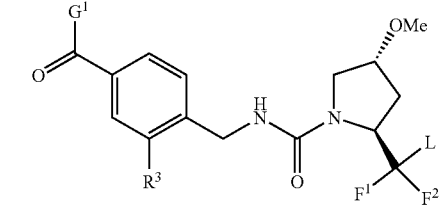 | H | NHBn | 568 |
| 106 | 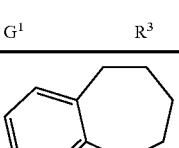 | \multicolumn{2}{l}{OCH₂CH₂O} | 558.3 |
TABLE I
Examples 107–124
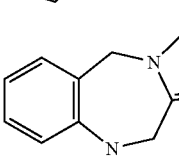
| Ex. | G¹ | R³ | F¹ | F² | L | M + H⁺ |
|---|---|---|---|---|---|---|
| 107 | (benzazepine) | Me | =O | | NMe₂ | 493.5 |
| 108 | (pyrrolo-benzodiazepine) | Me | =O | | NMe₂ | 530.3 |

TABLE I-continued

Examples 107–124

| Ex. | G¹ | R³ | F¹ | F² | L | M + H⁺ |
|---|---|---|---|---|---|---|
| 109 | (pyrido-benzodiazepine) | Me | =O | | NMe₂ | 543.4 |
| 110 | (triazolo-benzodiazepine) | Me | =O | | NMe₂ | 532.4 |
| 111 | (pyrido-benzoxazepine) | Me | =O | | NMe₂ | 544.3 |
| 112 | (N-isopropyl-benzodiazepine) | Me | =O | | NMe₂ | 536.4 |
| 113 | (benzodiazepine NH·HCl) | Me | =O | | NMe₂ | 494.5 |
| 114 | (benzoxazepine) | Cl | =O | | NMe₂ | 515.2 |
| 115 | (pyrrolo-benzodiazepine) | Cl | =O | | NMe₂ | 551.5 |
| 116 | (pyrrolo-benzodiazepine) | Me | =O | | NMeEt | 558.3 |
| 117 | (pyrrolo-benzodiazepine) | Me | =O | piperidine | | 570.3 |
| 118 | (pyrrolo-benzodiazepine) | Me | =S | | NMe₂ | 546.2 |
| 119 | (thieno-azepine) | Cl | =S | | NMe₂ | 535.1 |
| 120 | (thieno-benzoxazepine) | Cl | =S | | NMe₂ | 585.1 |
| 121 | (N-acetyl-thieno-benzodiazepine) | Me | =O | | NMe₂ | 590.2 |
| 122 | (thieno-benzodiazepine) | Me | =O | | NMe₂ | 548.2 |
| 123 | (benzodiazepine) | Me | =O | | NMe₂ | 494.3 |
| 124 | (N-ethyl-benzodiazepine) | Me | =O | | NMe₂ | 522.4 |

TABLE J

Examples 125–153

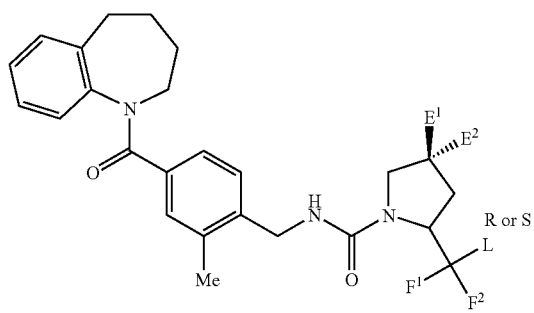

| Ex. | E$^1$ | E$^2$ | F$^1$ | F$^2$ | L | | M + H$^+$ |
|---|---|---|---|---|---|---|---|
| 125 | H | H | H | H | OMe | R | 436.4 |
| 126 | H | H | H | H | OMe | S | 436.2 |
| 127 | H | H | | =O | NMeEt | R | 477.2 |
| 128 | H | OPh | | =O | OMe | R | 542.3 |
| 129 | H | OPh | | =O | OH | RS | 528.3 |
| 130 | H | OPh | | =O | NMe$_2$ | RS | 555.3 |
| 131 | H | F | | =O | OH | R | 454.4 |
| 132 | OMe | OMe | | =O | OMe | R | 510.3 |
| 133 | OMe | OMe | | =O | OH | R | 496.2 |
| 134 | H | H | | =O | OtBu | R | 492.5 |
| 135 | H | H | | =O | OH | R | 436.3 |
| 136 | H | OH | | =O | OMe | R | 466.0 |
| 137 | H | OH | | =O | OEt | R | 480.2 |
| 138 | H | H | | =S | NMe$_2$ | R | 479.2 |
| 139 | H | OMe | | =O | OMe | R | 480.2 |
| 140 | H | H | | =O | OiPr | R | 478.2 |
| 141 | H | OH | | =O | OH | R | 452.1 |
| 142 | H | OBn | | =O | OiPr | R | 584.2 |
| 143 | H | OH | | =O | OiPr | R | 494.1 |
| 144 | H | OBn | | =O | NMe$_2$ | R | 569.2 |
| 145 | H | OMe | | =O | OH | R | 466.2 |
| 146 | H | OEt | | =O | NMe$_2$ | R | 507.3 |
| 147 | H | Cl | | =O | OMe | R | 484.1 |
| 148 | H | Cl | | =O | OH | R | 470.1 |
| 149 | H | Cl | | =O | NMe$_2$ | R | 497.2 |
| 150 | Cl | H | | =O | NMe$_2$ | R | 497.2 |
| 151 | H | F | | =O | OMe | R | 468.3 |
| 152 | H | F | | =O | NMe$_2$ | R | 481.3 |
| 153 | OMe | OMe | | =O | NMe$_2$ | R | 523.3 |

TABLE K

Examples 154–159

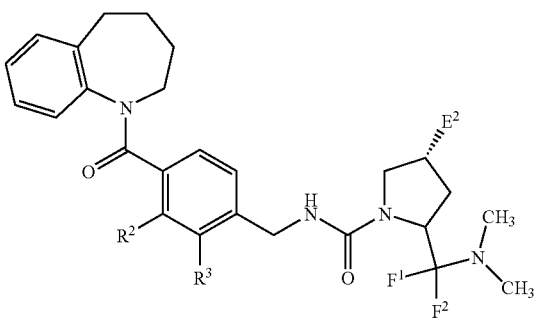

| Ex. | R$^2$ | R$^3$ | E$^2$ | F$^1$ | F$^2$ | M + H$^+$ |
|---|---|---|---|---|---|---|
| 154 | H | Cl | H | | =O | 483.4 |
| 155 | Me | H | H | | =O | 463.2 |
| 156 | Cl | H | H | | =O | 483.1 |
| 157 | H | Cl | H | | =S | 499.2 |
| 158 | H | Cl | OBn | | =O | 589.2 |
| 159 | H | Cl | OH | | =O | 499.2 |

TABLE L

Examples 160–164

| Ex. | R$^2$ | E$^2$ | M + H$^+$ |
|---|---|---|---|
| 160 | Cl | H | 489.1 |
| 161 | Me | H | 469.2 |
| 162 | Me | OH | 485.0 |
| 163 | Cl | OMe | 519.3 |
| 164 | Me | OMe | 499.3 |

TABLE M

Examples 165–170

| Ex. | R$^4$ | E$^2$ | F$^1$ | F$^2$ | V | M + H$^+$ |
|---|---|---|---|---|---|---|
| 165 | H | H | | =O | S | 479.4 |
| 166 | H | OH | | =O | S | 495.0 |
| 167 | H | H | | =S | S | 495.1 |
| 168 | Me | H | | =O | O | 477.2 |
| 169 | H | OBn | | =O | S | 585.2 |
| 170 | H | OBn | | =S | O | 585.0 |

TABLE N

Examples 171–177

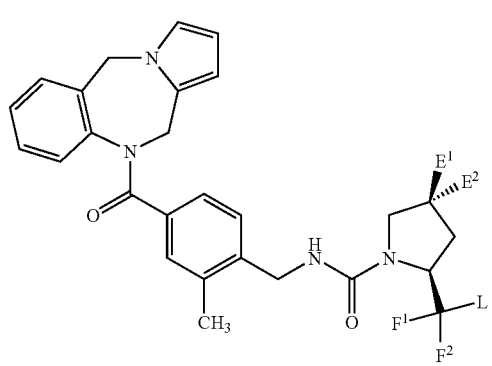

| Ex. | E¹ | E² | F¹ | F² | L | M + H⁺ |
|---|---|---|---|---|---|---|
| 171 | H | H | | =S | NMe₂ | 516.2 |
| 172 | H | OBn | | =O | NMe₂ | 606.3 |
| 173 | H | OH | | =O | NMe₂ | 507.3 |
| 174 | OMe | OMe | | =O | OMe | 547.3 |
| 175 | —OCH₂CH₂O— | | | =O | OMe | 545.3 |
| 176 | —OCH₂CH₂O— | | | =O | NMe₂ | 558.3 |
| 177 | —SCH₂CH₂S— | | | =O | NMe₂ | 590.2 |

TABLE O

Examples 178–182

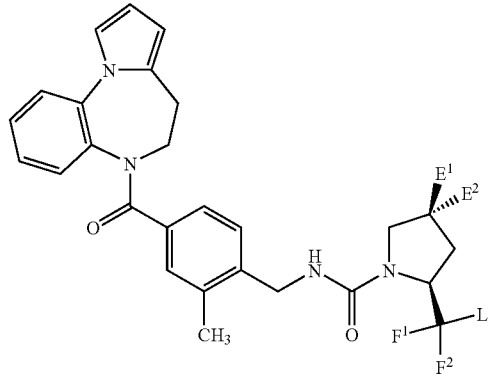

| Ex. | E¹ | E² | F¹ | F² | L | M + H⁺ |
|---|---|---|---|---|---|---|
| 178 | H | OH | | =O | NMe₂ | 516.1 |
| 179 | H | H | | =S | NMe₂ | 516.2 |

TABLE O-continued

| | | | | | |
|---|---|---|---|---|---|
| 180 | H | OMe | =O | NMe₂ | 530.4 |
| 181 | —OCH₂CH₂O— | | =O | OMe | 545.3 |
| 182 | —OCH₂CH₂O— | | =O | OH | 531.3 |

TABLE P

Examples 183–190

| Ex. | A¹⁰ | R³ | E² | F¹ | F² | M + H⁺ |
|---|---|---|---|---|---|---|
| 183 | O | Me | H | | =O | 519.3 |
| 184 | NMe | Me | H | | =O | 532.33 |
| 185 | NMe | Me | OH | | =O | 548.1 |
| 186 | NMe | Me | OMe | | =O | 562.3 |
| 187 | O | Me | OMe | | =O | 549.2 |
| 188 | NMe | Me | OMe | | =S | 578.2 |
| 189 | O | Cl | OMe | | =O | 569.1 |
| 190 | O | Me | OMe | | =S | 565.2 |

TABLE Q

Representative NMR data

Ex. No ¹H NMR(CDCl₃)

28  δ 1.40–1.60(1H, m), 1.84–2.20(3H, m), 2.15(3H, s), 2.40–2.54(2H, m), 2.58–2.92(4H, m), 2.94–3.10(1H, m), 3.65(3H, s), 4.30(2H, d, J=5.6Hz), 4.99(1H, d, J=12.9Hz), 5.90(1H, s), 6.62(1H, d, J=7.9Hz), 6.78–6.96(3H, m), 7.00–7.16(2H, m), 7.21(1H, m)ppm 29  δ 1.48–1.70(1H, m), 1.96–2.16(3H, m), 2.26(3H, s), 2.78–3.18(3H, m), 3.98(3H, s), 4.50(2H, d, J=6.8Hz), 5.08(1H, d, J=12.7Hz), 6.72(1H, d, 7.6Hz), 6.88–7.06(3H, m), 7.18(1H, t, J=7.6Hz), 7.22–7.36(2H, m)ppm TABLE Q-continued Representative NMR data

| Ex. No | $^1$H NMR(CDCl$_3$) |
|---|---|
| 30 | δ 1.40–1.62(1H, m), 1.84–2.24(3H, s), 2.17(3H, s), 2.70–3.10(3H, m), 4.40(2H, d, J=5.9Hz), 4.99(1H, d, J=12.9Hz), 6.63(1H, d, J=7.6Hz), 6.80–6.98(3H, m), 7.02–7.28(3H, m), 7.38(1H, brs)ppm |
| 31 | δ 1.42–1.62(1H, m), 1.84–2.28(8H, m), 2.30–2.50(4H, m), 2.70–2.94(2H, m), 2.96–3.12(1H, m), 3.65(3H, s), 4.31(2H, d, J=5.3Hz), 4.99(1H, d, J=13.9Hz), 5.75(1H, br s), 6.63(1H, d, J=7.6Hz), 6.78–6.98(3H, m), 7.02–7.16(2H, m), 7.21(1H, d, J=6.6Hz)ppm |
| 32 | δ 1.18(3H, t, J=7.3Hz), 1.38–1.55(1H, m), 1.80–2.10(3H, m), 1.95(3H, s), 2.60–2.98(3H, m), 3.84(2H, s), 4.04(2H, s), 4.07(2H, q, J=7.3Hz), 4.87–4.92(1H, m), 5.73(2H, brs), 6.50(1H, d, J=7.3Hz), 6.63–6.97(5H, m), 7.11(1H, d, J=7.3Hz)ppm |
| 33 | δ 1.30–1.50(1H, m), 1.75–2.05(3H, m), 1.94(3H, s), 2.60–2.98(3H, m), 3.59(2H, br s), 4.01(2H, br s), 4.80–4.85(1H, m), 6.05(2H, br s), 6.53(1H, d, J=7.2Hz), 6.75–6.99(5H, m), 7.11(1H, d, J=7.2Hz)ppm. |
| 34 | δ 1.40–1.60(1H, m), 1.80–2.00(2H, m), 2.00–2.20(3H, s), 2.60(3H, d, J=4.0Hz), 2.65–3.05(3H, m), 3.60(2H, d, J=4.0Hz), 4.15(2H, d, J=4.0Hz), 4.90–5.00(1H, m), 6.10–6.30(2H, m), 6.60(1H, d, J=8.0Hz), 6.70–7.20 (8H, m)ppm |
| 35 | δ 1.39–1.50(1H, m), 1.86–2.10(3H, m), 2.07(3H, s), 2.57(3H, s), 2.60–3.00(3H, m), 2.85(3H, s), 3.95(2H, d, J=4.0Hz), 4.16(2H, d, J=5.6Hz), 4.90–5.00(1H, m), 5.74(1H, br s), 6.11(1H, br s), 6.54(1H, d, J=7.6Hz), 6.78–7.18(6H, m)ppm |
| 36 | δ 1.38–1.50(1H, m), 1.80–2.00(3H, m), 2.00(3H, s), 2.60–3.00(3H, m), 3.64(3H, s), 3.90(2H, s), 4.10(2H, s), 4.85–4.95(1H, m), 6.52(1H, d, J=7.2Hz), 6.67–7.02(7H, m), 7.13(1H, d, J=6.2Hz)ppm |
| 37 | δ 1.40–1.76(2H, m), 1.84–2.16(2H, m), 2.29(3H, s), 2.66–3.10(3H, s), 3.95(2H, s), 4.56(2H, s), 4.99(1H, d, J=13.9Hz), 5.59(1H, br s), 6.63 (1H, d, J=7.9Hz), 6.80–6.98(3H, m), 7.00–7.12(2H, m), 7.20(1H, d, J=7.3Hz)ppm |
| 38 | δ 1.70–1.86(3H, m), 1.96–2.08(2H, m), 2.44–2.56(2H, m), 2.60–2.72(2H, m), 2.86–2.98(2H, m), 3.67(3H, s), 3.85(1H, br s), 4.44(2H, d, J=5.9Hz), 6.18(1H, d, J=5.3Hz), 6.28(1H, br s), 6.68(1H, d, J=5.3Hz), 7.03(1H, d, J=7.6Hz), 7.15(1H, d, J=7.6Hz)ppm |
| 39 | δ 1.35–1.55(1H, m), 1.74–2.10(3H, m), 2.11(3H, s), 2.17–2.35(1H, m), 2.60–2.82(2H, m), 2.86(3H, s), 2.90–3.14(2H, m), 3.05(3H, s), 3.26(1H, dd, J=14.9&7.2Hz), 3.40–3.53(1H, m), 3.64–3.84(1H, m), 4.03–4.19(1H, m), 4.29–4.42(1H, m), 4.55–4.68(1H, m), 4.74–4.81(1H, m), 4.85–4.98(1H, m), 6.58(1H, d, J=7.7Hz), 6.75–6.89(2H, m), 6.91–7.06(3H, m), 7.16(1H, d, J=6.5Hz), 7.93–8.03(1H, m)ppm |
| 40 | δ 1.65–1.80(2H, m), 1.85–2.00(3H, m), 2.05–2.25(1H, m), 2.10(3H, s), 2.80–3.10(3H, m), 2.85(3H, s), 3.00(3H, s), 3.40–3.30(1H, m), 3.45–3.55(1H, m), 3.65–3.95(1H, m), 4.00–4.10(1H, m), 4.30–4.55(1H, m), 4.91(1H, t, J=7.7Hz), 5.15–5.30(1H, m), 6.10–6.20(1H, m), 6.55–6.65(1H, m), 6.85–7.50(5H, m)ppm |
| 66 | δ 1.17(6H, d, J=6.3Hz), 1.20–1.24(1H, m), 1.80–2.10(3H, m), 2.00(3H, s), 2.60–3.00(3H, m), 3.85(2H, d, J=5.3Hz), 4.10(2H, d, J=4.9Hz), 4.82–4.85(1H, m), 4.96(1H, sept, J=6.2Hz), 5.33(1H, t, J=5.2Hz), 5.43(1H, t, J=4.9Hz), 6.52(1H, d, J=7.6Hz)ppm |
| 67 | δ 1.38–1.42(1H, m), 1.38(9H, s), 1.78–2.10(3H, m), 1.97(3H, s), 2.60–3.00(3H, m), 3.78(2H, s), 4.07(2H, s), 4.89–4.94(1H, m), 5.50(2H, br s), 6.51(1H, d, J=7.9Hz), 6.64–6.98(5H, m), 7.12(1H, d, J=7.7Hz)ppm |
| 68 | δ 1.38–1.50(1H, m), 1.80–2.06(3H, m), 2.60–3.00(3H, m), 2.70(3H, s), 2.87(3H, s), 3.96(2H, d, J=4.0Hz), 4.27(2H, d, J=6.0Hz), 4.85–4.95(1H, m), 5.98(1H, t, J=6.0Hz), 6.14(1H, t, J=4.0Hz), 6.55(1H, d, J=7.6Hz), 6.80–7.16(6H, m)ppm |
| 69 | δ 1.25(3H, t, J=7.0Hz), 1.40–1.60(1H, m), 1.85–2.20(3H, m), 2.04(3H, s), 2.45(2H, t, J=6.27Hz), 2.65–3.10(3H, m), 3.30–3.50(2H, m), 4.00–4.20(4H, m), 4.90–5.00(1H, m), 5.50–5.70(2H, m), 6.50–7.20(7H, m)ppm |
| 70 | δ 1.20–1.45(1H, m), 1.65–2.05(3H, m), 1.95(3H, s), 2.05–2.25(2H, m), 2.50–3.00(3H, m), 3.00–3.20(2H, m), 3.85–4.05(2H, m), 4.65–4.90(1H, m), 5.80–6.20(1H, br s), 6.40–7.20(9H, m)ppm |

Example 191

Determination of V$_2$r Ceptor Agonist Activity in Vitro

Agonist activity was determined for all compounds and is reported as an EC$_{50}$ value, being that concentration of compound necessary to cause a half-maximal cellular activation. All the compounds had EC$_{50}$ values of 10 μM or less, and typical results are listed in Table R.

TABLE R

EC$_{50}$ values for typical compounds

| Compound of Example | EC$_{50}$ (nM) |
|---|---|
| 1 | 39 |
| 2 | 160 |

TABLE R-continued

EC$_{50}$ values for typical compounds

| Compound of Example | EC$_{50}$ (nM) |
|---|---|
| 3 | 300 |
| 4 | 300 |
| 5 | 150 |
| 6 | 47 |
| 7 | 24 |
| 8 | 220 |
| 9 | 50 |
| 10 | 4 |
| 11 | 21 |
| 12 | 50 |
| 13 | 38 |
| 14 | 240 |
| 15 | 44 |
| 16 | 16 |
| 17 | 16 |
| 18 | 17 |
| 19 | 40 |
| 20 | 17 |
| 21 | 180 |
| 22 | 1000 |
| 23 | 40 |
| 24 | 92 |
| 25 | 280 |
| 26 | 10 |
| 27 | 23 |

Example 192

Determination of Antidiuretic Activity in Vivo

The Brattleboro rat is a recognised model for vasopressin deficiency (for a review see FD Grant, "Genetic models of vasopressin deficiency", Exp. Physiol. 85, 203S–209S, 2000). The animals do not secrete vasopressin and consequently produce large volumes of dilute urine. Compounds of the invention were administered to Brattleboro rats (0.1–10 mg/kg p.o. in methylcellulose. Urine was callected hourly and volumes were compared with control animals. Animals had free access to food and water throughout the experiment. Representative results are given in Table S. Results for Desmopressin are given for comparison.

TABLE S

Antidiuretic activity

| Compound of Example | Dose | % inhibition of urine output (at 1 hour) |
|---|---|---|
| 32 | 1 mg/kg | 74 |
| 33 | 1 mg/kg | 38 |
| 35 | 1 mg/kg | 45–82 |
| 39 | 1 mg/kg | 82 |
| 62 | 1 mg/kg | 58 |
| 88 | 1 mg/kg | 60 |
| 103 | 1 mg/kg | 63 |
| 107 | 1 mg/kg | 84 |
| 119 | 1 mg/kg | 68 |
| 163 | 1 mg/kg | 90 |
| Desmopressin | 0.1 mg/kg | 37 |
|  | 1 mg/kg | 100 |
|  | 10 mg/kg | 100 |

Example 193

Pharmaceutical Composition for Tablet

Tablets containing 100 mg of the compound of Example 39 as the active agent are prepared from the following:

| | |
|---|---|
| Compound of Example 39 | 200.0 g |
| Corn starch | 71.0 g |
| Hydroxypropylcellulose | 18.0 g |
| Carboxymethylcellulose calcium | 13.0 g |
| Magnesium stearate | 3.0 g |
| Lactose | 195.0 g |
| Total | 500.0 g |

The materials are blended and then pressed to give 2000 tablets of 250 mg, each containing 100 mg of the compound of Example 39.

The foregoing Examples demonstrate that compounds within the scope of the invention are readily prepared using standard chemical techniques, and that these compounds have the biological properties that would be expected of V$_2$ receptor agonists. In particular, the compounds are potent antidiuretic in an animal model of vasopressin deficiency. Thus it is clear that they may be useful in the treatment of human diseases that are currently treatable with Desmopressin, such as central diabetes insipidus, nocturnal enuresis and nocturia. It has further been suggested that antidiuretics such as Desmopressin may be useful in certain types of urinary incontinence. These arguments would also extend to the compounds of the present invention.

Desmopressin is also used in the treatment of certain coagulation disorders. There is good evidence to suggest that this action is also mediated through the V$_2$ receptor (see for example J E Kaufmann et al., "Vasopressin-induced von Willebrand factor secretion from endothelial cells involves V$_2$ receptors and CAMP", J. Clin. Invest. 106, 107–116, 2000; A Bernat et al., "V$_2$ receptor antagonism of DDAVP-induced release of hemostasis factors in conscious dogs", J. Pharmacol. Exp. Ther. 282, 597–602, 1997), and hence it would be expected that the compounds of the present invention should be useful pro-coagulants. The scope of the present invention is further defined in the following claims.

The invention claimed is:

1. A compound according to formula 1 or 2, or a tautomer or a pharmaceutically acceptable salt thereof:

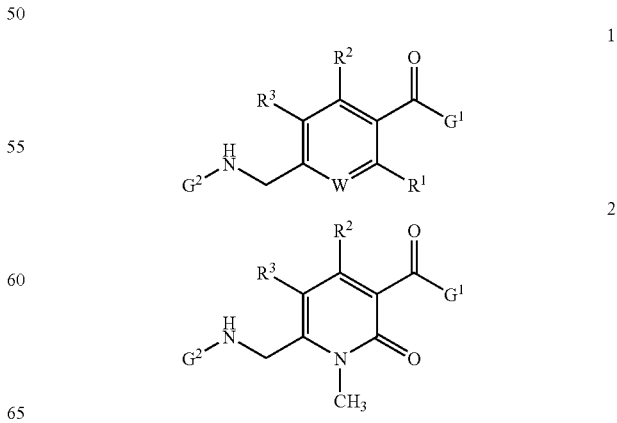

wherein:
W is either N or C—R⁴;
R¹–R⁴ are independently selected from H, F, Cl, Br, alkyl, CF₃, phenyl, OH, O-alkyl, NH₂, NH-alkyl, N(alkyl)₂, NO₂ and CN, or R² and R³ together can be —CH=CH—CH=CH—;
G¹ is a bicyclic fused azepine derivative according to formula 8:

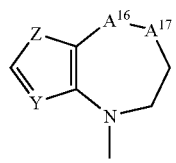

in which
A¹⁶ and A¹⁷ are both CH₂, or one of A¹⁶ and A¹⁷ is CH₂ and the other is selected from CH(OH), CF₂, O, SO_a and NR⁵;
R⁵ is selected from H, alkyl, CO-alkyl and (CH₂)_b R⁶;
R⁶ is selected from phenyl, pyridyl, OH, O-alkyl, NH₂, NH-alkyl, N(alkyl)₂, NO₂, CO₂H and CN;
a is 0, 1 or 2;
b is 1, 2, 3 or 4;
Y is CH or N;
Z is CH=CH or S; and
G² is a group according to formula 9:

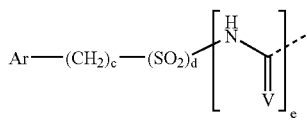

in which
Ar is selected from phenyl, pyridyl, naphthyl and mono- or polysubstituted phenyl or pyridyl wherein the substituents are selected from F, Cl, Br, alkyl, OH, O-alkyl, NH₂, NH-alkyl, N(alkyl)₂, NO₂ and CN;
V is O, N—CN or S;
c is 0 or 1;
d is 0 or 1; and
e is 0 or 1,
provided that d and e are not both 0.

2. A compound according to claim 1, or a tautomer or pharmaceutically acceptable salt thereof, wherein the compound is a compound according to general formula 1.

3. A compound according to claim 2, or a tautomer or pharmaceutically acceptable salt thereof, wherein W is C—R⁴.

4. A compound according to claim 3, or a tautomer or pharmaceutically acceptable salt thereof, wherein at least one of R¹–R⁴ is not H.

5. A compound according to claim 4, or a tautomer or pharmaceutically acceptable salt thereof, wherein one of R¹–R⁴ is methyl, F or Cl and the others are all H.

6. A compound according to claim 1, or a tautomer or pharmaceutically acceptable salt thereof, wherein A¹⁷ is CH₂.

7. A compound according to either claim 1, or a tautomer or pharmaceutically acceptable salt thereof, wherein A¹⁶ is CH₂.

8. A compound according to claim 1, or a tautomer or pharmaceutically acceptable salt thereof, wherein Ar is mono- or polysubstituted phenyl.

9. A compound according to either claim 1, or a tautomer or pharmaceutically acceptable salt thereof, wherein Ar is phenyl substituted with at least two halogen atoms selected from F and Cl.

10. A compound according to any of claims 1, or a tautomer or pharmaceutically acceptable salt thereof, wherein Ar is 2,6-difluorophenyl.

11. A compound according to claim 6, or a tautomer or pharmaceutically acceptable salt thereof, wherein A¹⁶ is CH₂.

12. A compound according to claim 8, or a tautomer or pharmaceutically acceptable salt thereof, wherein Ar is phenyl substituted with at least two halogen atoms selected from F and Cl.

13. A compound according to claim 1, or a tautomer or pharmaceutically acceptable salt thereof, selected from
1-(4-[3-(2-Chloro-6-fluorophenyl)ureidomethyl]-3-methylbenzoyl)-2,3,4,5-tetrahydro-1H-1-benzazepine,
1-(4-[3-(2,6-Difluorophenyl)ureidamethyl]-3-methylbenzoyl)-5-(3-pyridyl)methyl-2,3,4,5-tetrahydro-1H-1,5-benzodiazepine,
1-(3-Chloro-4-[3-(2-chloro-6-fluorophenyl)ureidomethyl]benzoyl)-5-ethyl-2,3,4,5-tetrahydro-1H-1,5-benzodiazepine,
4-(3-Chloro-4-[3-(2,6-difluorophenyl)ureidomethyl]benzoyl-5,6,7,8-tetrahydrothieno[3,2-b]azepine, and
1-(2-Methyl-4-(5-(3-pyridylmethyl)-2,3,4,5-tetrahydro-1, 5benzodiazepin-1-ylcarbonyl)benzyl)-3-(methyloxycarbonylmethyl)urea.

14. A pharmaceutical composition which comprises, as an active agent, a compound according to claim 1.

15. A method of treating a condition selected from the group consisting of nocturnal enuresis, nocturia and diabetes insipidus, which method comprises administering to a person in need of such treatment an effective amount of a composition according to claim 14.

16. A method for the control of urinary incontinence, which method comprises administering to a person in need of such treatment an effective amount of a composition according to claim 14.

17. A method for the control of urinary incontinence according to claim 16, wherein the treatment results in voiding postponement.

18. A method for the treatment of bleeding disorders, which method comprises administering to a person in need of such treatment an effective amount of a composition according to claim 14.

* * * * *